(12) United States Patent
Whitaker et al.

(10) Patent No.: US 12,024,796 B2
(45) Date of Patent: Jul. 2, 2024

(54) VARIABLE HEAVY CHAIN ONLY LIBRARIES, METHODS OF PREPARATION THEREOF, AND USES THEREOF

(71) Applicant: Tavotek Biotherapeutics (Hong Kong) Limited, Shung Wan (HK)

(72) Inventors: Brian Whitaker, Downington, PA (US); Mark Anthony Tornetta, Collegeville, PA (US); Mark L. Chiu, Paoli, PA (US); Man-Cheong Fung, Ringoes, NJ (US)

(73) Assignee: Tavotek Biotherapeutics (Hong Kong) Limited, Shung Wan (HK)

( * ) Notice: Subject to any disclaimer, the term of this patent is extended or adjusted under 35 U.S.C. 154(b) by 1 day.

(21) Appl. No.: 17/540,612

(22) Filed: Dec. 2, 2021

(65) Prior Publication Data
US 2022/0177870 A1    Jun. 9, 2022

Related U.S. Application Data

(60) Provisional application No. 63/120,842, filed on Dec. 3, 2020.

(51) Int. Cl.
| | |
|---|---|
| *C40B 40/08* | (2006.01) |
| *A61K 47/65* | (2017.01) |
| *C07K 16/00* | (2006.01) |
| *C12N 15/10* | (2006.01) |
| *C40B 40/10* | (2006.01) |

(52) U.S. Cl.
CPC .............. *C40B 40/10* (2013.01); *A61K 47/65* (2017.08); *C07K 16/005* (2013.01); *C12N 15/1037* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 10,189,894 B2 | 1/2019 | Vasquez et al. | |
| 2011/0076752 A1 | 3/2011 | Wu et al. | |

OTHER PUBLICATIONS

Chen et al. (2008) Journal of Molecular Biology vol. 382 pp. 779 to 789.*

(Continued)

*Primary Examiner* — Christian C Boesen
(74) *Attorney, Agent, or Firm* — Finnegan, Henderson, Farabow, Garrett & Dunner, LLP

(57) ABSTRACT

The present disclosure relates to designs and applications of Variable Heavy Only (VHO) domain regions. The present disclosure provides a VHO library of polynucleotides encoding VHO domains, wherein the VHO domains are designed based on the Vh domain of a human Vh family, and a method of generating the VHO library. The present disclosure also provides a phage library displaying the VHO domains encoded by the VHO library through the use of M13 bacteriophage minor coat proteins such as pIX and pVII and a method of generating the phage library. The present disclosure also provides a method of screening the phage library to identify VHO candidates that are capable of binding a target of interest.

31 Claims, 10 Drawing Sheets
Specification includes a Sequence Listing.

(56) References Cited

OTHER PUBLICATIONS

Chen et al., "Construction of a large phage-displayed human antibody domain library with a scaffold based on a newly identified highly soluble, stable heavy chain variable domain," J Mol Biol., 382(3):779-789 (2008).
International Search Report and Written Opinion of the International Searching Authority, PCT/US21/61574, dated Mar. 15, 2022, 8 pages.

* cited by examiner

Figure 3A: Pairwise Identity – 79%
Figure 3 B. Pairwise Identity – 81%

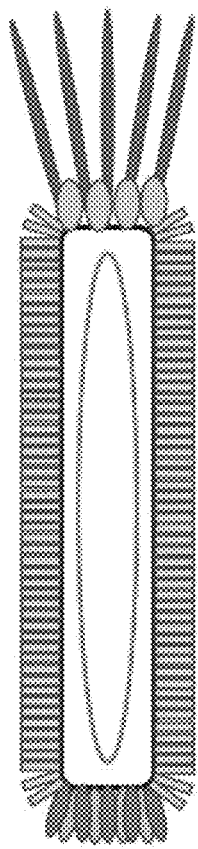
Figure 4A
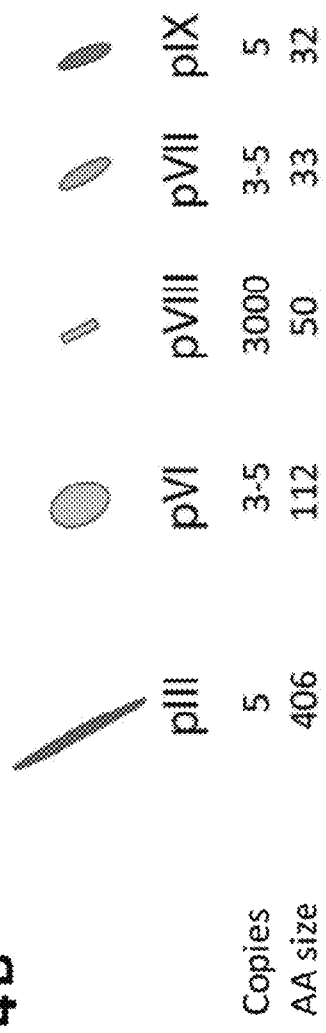
Figure 4B
Figure 4

Figure 5A
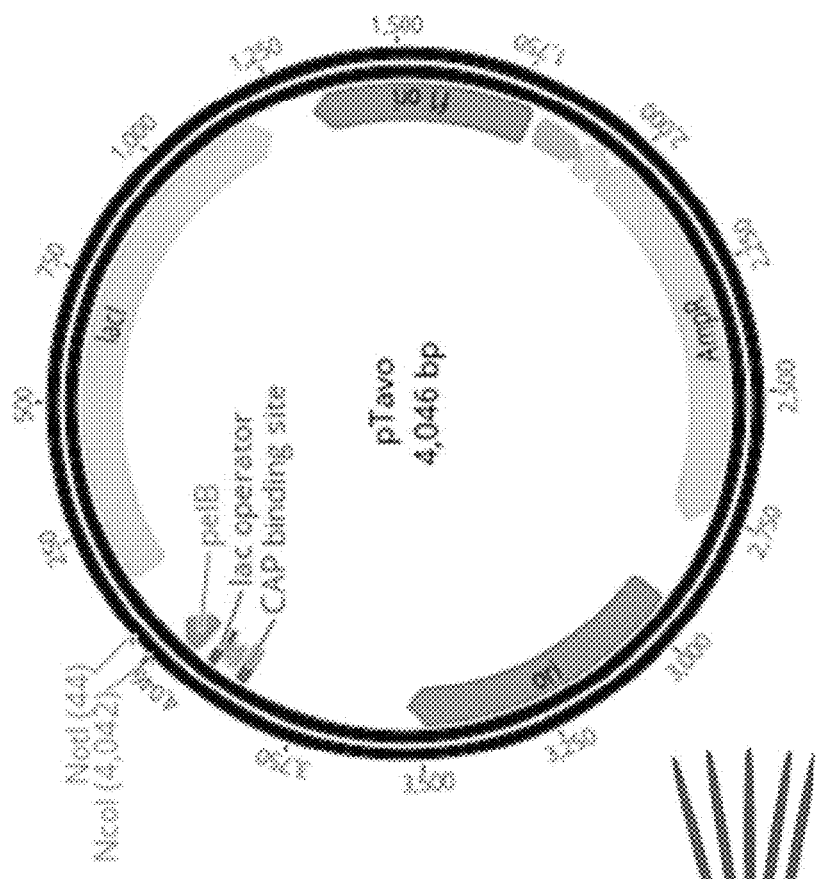
Figure 5B
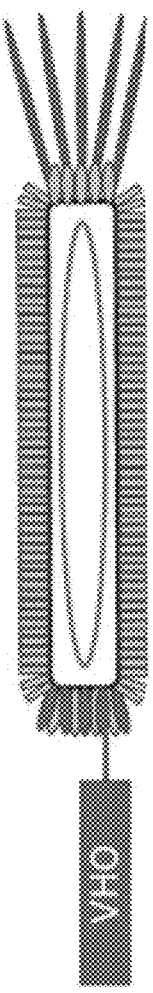
Figure 5C
Figure 5

Figure 6

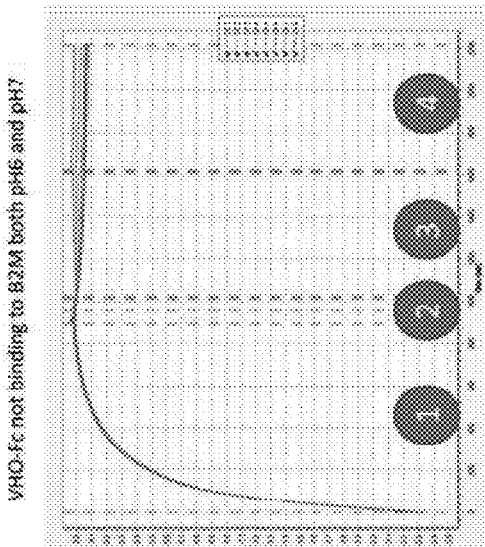
Figure 7A
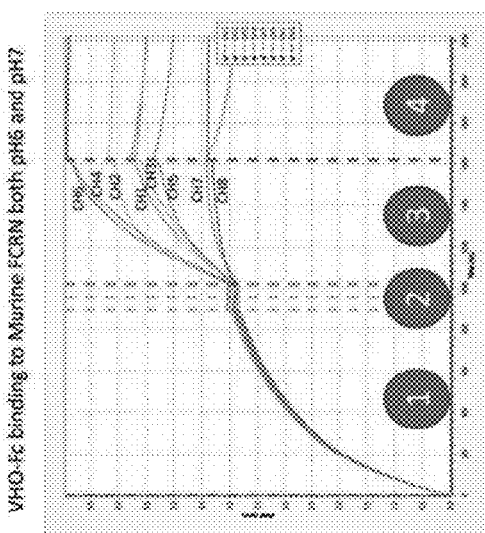
Figure 7B
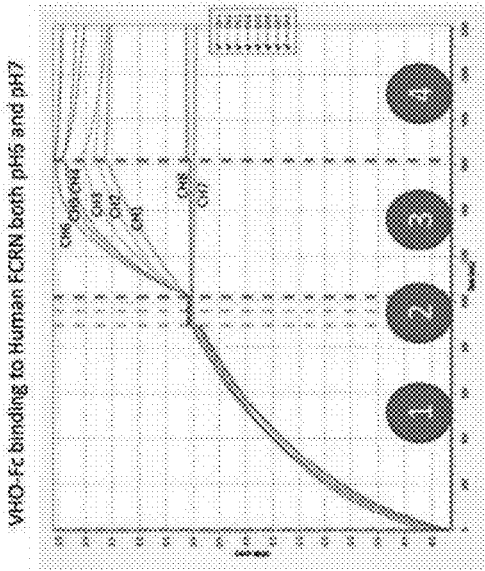
Figure 7C
Figure 7

| From 5 target projects the number of hits per candidate characterization step | | | | | |
|---|---|---|---|---|---|
| HCDR3 lengths designed in the phage libraries | 9-14 | 9-14 | 9-16 | 9-16 | 9-16 |
| # of Candidates evaluated | 42 | 33 | 24 | 51 | 40 |
| VHO-Fc conversions | 42 | 24/33 | 24/24 | 49/51 | 38/40 |
| Confirmed binding | 33/42 | 16/24 | 17/24 | 19/27 | >29/40 |
| Species cross-reactivity | 17/33 | 0/16 | 10/17 | 10/19 | >11/>29 |
| # Epitope groups | 6 | 3-4 | 8 | >7 | >6 |
| Inhibitory activity | nd | nd | 7 | na | na |
| Binding to cells | na | na | 5 | 8 | nd |
| nd=not done | | | na=not applicable | | |

Figure 9

VARIABLE HEAVY CHAIN ONLY LIBRARIES, METHODS OF PREPARATION THEREOF, AND USES THEREOF

CROSS-REFERENCE TO RELATED APPLICATION

This application claims the priority of Provisional Application No. 63/120,842, filed on Dec. 3, 2020, the content of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 2, 2021, is named 15271_0007-00000_SL and is 19,819 bytes in size.

FIELD OF THE DISCLOSURE

The present disclosure relates to designs and applications of Variable Heavy Only (VHO) domain regions, which can serve as selective binding moieties and can be used as therapeutic molecules and/or diagnostic reagents. The present disclosure also relates to methods of generating diverse VHO degenerate libraries, and methods of displaying degenerate VHO libraries using coat proteins of bacteriophages.

BACKGROUND OF THE DISCLOSURE

VHH (variable heavy homodimers) or single domain antibodies have been studied for some time and are being used in medicine (Muyldermans 2013); (Belanger, Iqbal et al. 2019). The camelid Heavy chain antibodies (HcAb) are found in Camelidae family (llama, camel, alpaca, etc.), and similar Variable New Antigen Receptor (VNAR) molecules are found in Chondrichthyes and Cyclostomata classes that include sharks and lampreys. The VHH most studied and used recombinantly to date are those from llamas and camels (Arbabi-Ghahroudi 2017). References made herein to the camel/llama family refer to the members of the Camelidae family. The Camelidae family antibodies are heavy chain only molecules sized at 70-90 kDa compared to human antibodies (IgG), which contain both heavy and light chains at 150-160 kDa in size (see FIG. 1A). The camel and llama antibodies consist, respectively, of 3 domains: variable domain, constant domain 2, and constant domain 3. The variable domain, like most antibodies, has 3 hypervariable loops with 4 framework regions in between those hypervariable loops. The variable region of a camel or llama antibody is the site for binding to foreign proteins during a humoral response. Like human antibodies, the diversity of paratope is defined by the hypervariable regions or complimentary determining regions (CDR) (Mitchell and Colwell 2018).

The Vh domains of camel and llama antibodies have been used to engineer single domain and nanobody molecules (Arbabi-Ghahroudi 2017). These molecules are ~15 kDa in size and have higher thermal stability compared to IgG (McConnell, Spasojevich et al. 2013). Because of these biophysical attributes, the single domain molecules provide an advantage for manufacturing and development (Tonikian and Sidhu 2012) (Ewert, Cambillau et al. 2002) (Harmsen and De Haard 2007). These attributes also provide advantages for more unique diagnostic and therapeutic applications. They can be engineered to pass through cell membranes, to cross the blood brain barrier, and to serve as alternative biologic delivery systems (Herce, Schumacher et al. 2017) (Bruce, Lopez-Islas et al. 2016). Examples of alternative drug delivery using single domains include adapting them with nanoparticles for guided systemic delivery (Yang, Moynihan et al. 2018) (Slastnikova, Ulasov et al. 2018) and efficient intranasal delivery (Gomes, Cabrito et al. 2018). These molecules can also be designed as fluorescent protein fusions to serve as imaging diagnostics (Li, Bourgeois et al. 2012). Some disease targets, e.g., viruses, possess size constraints for IgGs, and therefore smaller protein therapeutics such as single domains are needed. (Wrapp, De VLieger et al. 2020) (Wilken and McPherson 2018).

The camel and llama antibody variable regions have protein sequence homology to human Vh domains (Mitchell and Colwell 2018), (Herold, John et al. 2017), (Muyldermans 2013), (Strohl et al., (2012), Woodhead Publishing). FIG. 1A shows the structures of human IgG and camelid antibodies. The consensus translations of the V gene segments for human, llama, and camel are aligned in FIG. 1(B) showing their amino acid sequence similarity (SEQ ID NO: 1-4). CDR3 is not shown in FIG. 1(B) because that is where the most diversity of an antibody resides. FIG. 2 shows a tree-based alignment of human Vh families to both camel and llama Vh families obtained from IMGT (the international ImMunoGeneTics information system) (http://www.imgt.org/IMGTrepertoire/Proteins/taballeles/human/IGH/IGHV/Hu_IGHVall.html). The grouping shows the human family Vh3 to be most similar in sequence homology to both camel and llama VH, but not so much with the other human Vh families. FIG. 3 shows further sequence homology within the human Vh3 sub-families.

The human Vh3 (also referred to as Vh3) family is the most prevalent one found during a human humoral response when immunized, as well as reflective of the distribution of antibodies in development (Joyce, Burton et al. 2020) (Longo, Rogosch et al. 2017). This family is also found to be the most represented in the human repertoire (Tiller, Schuster et al. 2013). Even though camel/llama single Vh domains are similar to human Vh domains of antibodies, they are also quite distinct. These differences may create immunogenic effects that limit the efficacy of diagnostic and therapeutic treatments using camel/llama single Vh domains.

Certain researchers have based their phage libraries from camel, llama, or alpaca antibody scaffolds. Lately, Twist Bioscience used scaffolds based on a mix of sequences of human and one of the other species (camel, llama, and alpaca). The sdAb (single domain antibodies) review by Rossotti et al. (2021) concluded that immunogenicity and anti-drug antibody responses (ADA) to sdAbs occurred from the intrinsic non-human sequences that resulted in the aggregation properties.

The present disclosure describes using human Vh regions in place of Camelid-derived VHH-based molecules, to generate single domain-based diagnostic or therapeutic compounds. For example, the present disclosure describes using the Vh regions of the human antibody Vh3 family to generate single domain-based therapeutic compounds. Such single domain-based therapeutic compounds may have improved stability and/or improved therapeutic index than single domain-based therapeutic compounds derived from other human antibody Vh families.

SUMMARY OF THE DISCLOSURE

The present disclosure provides a VHO (variable heavy only) platform to generate single domain-based therapeutic compounds, e.g., sdAb, nanobodies (Nb), and VHH type of antibodies. In one embodiment, the present disclosure provides a VHO library (also referred to herein as a TavoSelect library) based on the human variable domain of a human Vh family, such as the gene family Vh3. For example, the Vh regions of the human antibody Vh3 family can be used as a scaffold for creating VHO libraries.

In one embodiment, the present disclosure provides a VHO library based on human variable domain germlines that are homologous by amino acid sequence and/or similar in canonical structure to the Vh domains of a human Vh family. In one embodiment, the present disclosure provides a VHO library of polynucleotides encoding diverse VHO domains, wherein the VHO domains have sequence homology and/or canonical homology with the Vh domain of a human Vh family, such as the gene family Vh3. For example, a canonical structure can include 3D modeling of human antibody sequences found at the IMGT (the international ImMunoGeneTics information system) or any other source such as Kabat database or V Base database.

In one embodiment, the present disclosure provides a phage library that is capable of displaying diverse VHO domains or displays diverse VHO domains (herein referred to as "a VHO phage library"). In one embodiment, a VHO library is assembled on a coat protein on a bacterial phage, such as M13 phage. In one embodiment, a VHO library is assembled by way of genetic fusion to the pIX and/or pVII coat protein of an M13 phage.

In one embodiment, the present disclosure provides a VHO phage library that is sufficiently robust to undertake a diverse selection or panning screening.

In one embodiment, the present disclosure provides a vector comprising a polynucleotide encoding any one of the VHO domains described herein.

In one embodiment, the present disclosure provides a method of preparing a VHO library, comprising providing polynucleotide sequences encoding the VHO domains described herein, and inserting the polynucleotide sequences into a vector, such as a phagemid and/or a plasmid.

In one embodiment, the present disclosure provides a method of preparing a VHO phage library, comprising transforming a bacterial cell culture with a VHO library described herein, allowing the bacterial cell culture to grow to a log phase, infecting the bacterial cell culture with a helper phage, and amplifying the bacterial cell culture.

In one embodiment, the present disclosure provides a method of screening a VHO phage library, e.g., by phage panning, to identify a VHO candidate of interest. In one embodiment, the present disclosure provides a method of identifying a VHO domain of interest that is capable of binding a target, comprising: creating a VHO library such as a VHO phage library as described herein, screening the VHO phage library using biopanning against the target to identify the VHO of interest. In one embodiment, the method further comprises sequencing the VHO of interest by NGS (next generation sequencing). In one embodiment, the method further comprises evaluating the binding affinity of the VHO of interest to the target, e.g., by ELISA, BLI, and/or SPR.

In one embodiment, VHO candidates of interest can be presented on a phage, expressed as a stand-alone protein, expressed as a fusion with an IgG or another soluble domain, or as a protein fusion to a cell surface protein such as a T or B cell receptor domain.

In one embodiment, a VHO as described herein can be connected to a human IgG Fc domain as a fusion. Such a fusion to an Fc domain may or may not possess a hinge region, or may or may not be fused to a constant heavy chain domain, or may or may not be fused to a constant light chain, either of the kappa or lambda families.

In one embodiment, the present disclosure provides a VHO of interest that can bind a target. In one embodiment, the present disclosure provides a protein that has greater than 50% identity to a VHO of interest. In one embodiment, the present disclosure provides a polynucleotide that encodes a protein that has greater than 50% identity to a VHO of interest.

In one embodiment, a VHO of interest is fused to a tag. The tag can be chosen from an Fc domain of any immunoglobulin family, poly histidine, and FLAG. For example, a VHO of interest is fused to a protein chosen from immunoglobulins, receptors, cell surface proteins, and fragments of the immunoglobulins, receptors, and cell surface proteins. For example, the VHO of interest can be expressed as a soluble protein, as a soluble protein fused to another protein (e.g., immunoglobulins), or as a fusion to any cell surface protein (e.g., receptors) in any bacterial cell (e.g., E. coli), any mammalian cell, yeast, or plant cell.

In one embodiment, the present disclosure provides a composition comprising a VHO of interest or a polypeptide comprising the VHO of interest, e.g., a fusion of the VHO of interest with another protein.

In one embodiment, the present disclosure provides a cell, e.g., a bacterial cell, comprising a vector as described herein.

BRIEF DESCRIPTION OF THE DRAWINGS

FIG. 3A shows amino acid sequence alignment of the human Vh3 sub-families and llama Vh families. FIG. 3B shows amino acid sequence alignment of the human Vh3 subfamilies and camelid Vh families.

FIG. 4A is a schematic drawing of an M13 filamentous bacteriophage and FIG. 4B illustrates the coat proteins that make up the exterior of an M13 phage.

FIG. 5 illustrates components that make up a VHO phage library. FIG. 5A is a schematic representation of a gene cassette showing DNA segments encoding a VHO fused to pIX (a coat protein of M13 phage), HIS (hexa-histidine residue (SEQ ID NO: 12)), and HA (hemagglutinin). FIG. 5B illustrates a phagemid/plasmid (herein referred to as pTAVO phagemid/plasmid), wherein a VHO gene cassette can be spliced into the pTAVO phagemid/plasmid in between the NcoI and NotI restriction sites. This phagemid/plasmid can be used for VHO gene expression and/or phage display libraries. FIG. 5C is a representative rendition of a VHO fused or displayed on the surface of an M13 phage.

FIG. 6 shows a tabulated distribution of 55 VHO candidates from a VHO phage library panned against three orthologs (human, cynomolgus monkey, and mouse) of the target, TNF (tumor necrosis factor). Each section (under "Human panning," "Cyno panning," and "Mouse panning," respectively) of the table in FIG. 6 shows a group of VHO candidates panned against the three respective ortholog targets (human, cyno cynomolgus monkey, and mouse TNF). Listed from the most copy sequence number to the least are the top 19 VHO candidates corresponding to the respective ortholog panning group. Within each section of a panning group are VHO sequences that were found in the other ortholog panning groups, thus indicating cross-reactivity of VHOs with the respective ortholog targets (e.g., VHO candidate Nos. 8 and 11 appear in both the "Human panning" group and the "Cyno panning" group, indicating VHO Nos. 8 and 11 may have cross-reactivity with human and cyno TNF). Cyno is an abbreviation of cynomolgus monkey.

FIG. 7 shows biolayer interferometry (GatorBio) binding kinetic runs performed with a set of VHO-Fc fusion molecules (VHO3-Fc, VHO4-Fc, and VHO5-Fc, comprising SEQ ID NOs: 7, 8, and 9 respectively), which were reactive to both human and mouse soluble FCRN proteins but not to beta-2-microglobulin (B2M). Odd numbered channels (denoted as CH1, CH3, CH5, and CH7) were run at pH 7 and the even numbered channels (denoted as CH2, CH4, CH6, and CH8) were run at pH 6. The biolayer interferometry binding sequence steps included (1)—binding of biotinylated FCRN (human and mouse) or B2M to the streptavidin coated sensor probe, (2)—washing to allow for baseline buffer exchanges, (3)—association of VHO-Fc analytes to the BLI sensor probe, (4)—dissociation of VHO-Fc analytes from FCRN or B2M on the BLI sensor probe. FIG. 7A showing VHO-Fc binding to human FcRn; FIG. 7B showing VHO-Fc binding to murine FcRn; FIG. 7C showing VHO-Fc not binding to beta-2 macroglobulin. On each of FIGS. 7A, 7B, and 7C, VHO3-Fc (comprising SEQ ID NO: 7) corresponds to CH1 and CH2; VHO4-Fc (comprising SEQ ID NO: 8) corresponds to CH3 and CH4; VHO5-Fc (comprising SEQ ID NO: 9) corresponds to CH5 and CH6; an IgG1 corresponds to CH7, and a negative control VHO2-Fc (comprising SEQ ID NO: 11) corresponds to CH8.

FIG. 9 shows a chart of five target VHO panning experiment results going through key steps of the VHO generation process. The first column of the table describes a key behavior, epitope binning, or grouping. The VHO library panning process can double the number of epitopes per number of candidates screened as compared to other sdAbs panning process in the art.

FIG. 10 discloses SEQ ID NOs: 23-24, and 24-27, respectively, in order of appearance.

DETAILED DESCRIPTION

Figure 1:
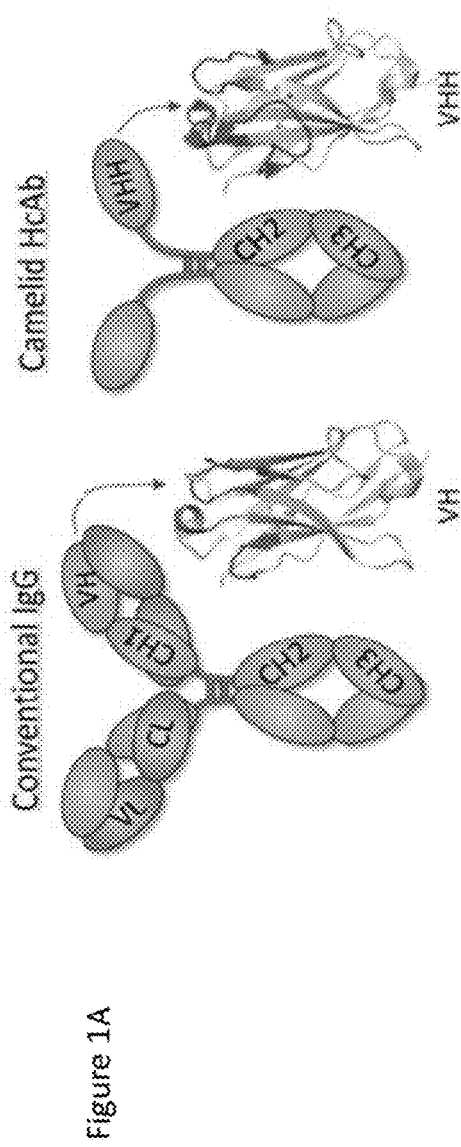
FIG. 1A shows structural models portraying an IgG and Camelid HcAb with 3D ribbon structures representing the variable heavy domains, denoted as Vh and VHH, respectively.
FIG. 1B shows a consensus sequence (SEQ ID NO: 1) aligned with the Vh domains of human (SEQ ID NO: 2), camel (SEQ ID NO: 3), and llama (SEQ ID NO: 4) antibodies including regions FR1, CDR1 (underlined), FR2, CDR2 (underlined), and FR3 according to IMGT nomenclature. The antibody images depicted on FIG. 1A can be found at https://www.frontiersin.org/files/Articles/288027/fimmu-08-00977-HTML/image_m/fimmu-08-00977-g001.jpg. CDR3 is not shown in FIG. 1B.

All publications, including but not limited to patents and patent applications, cited in this specification are herein incorporated by reference as though fully set forth. If certain content of a reference cited herein contradicts or is inconsistent with the present disclosure, the present disclosure controls.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein.

As used in this specification and the appended claims, the singular forms "a," "an," and "the" include plural referents unless the content clearly dictates otherwise. Thus, for example, reference to "a cell" includes a combination of two or more cells, and the like.

"Antibodies" is meant in a broad sense and includes immunoglobulin molecules including monoclonal antibodies including murine, human, humanized and chimeric monoclonal antibodies, antibody fragments, bispecific or multi-specific antibodies, dimeric, tetrameric, or multimeric antibodies, single chain antibodies, domain antibodies and any other modified configuration of the immunoglobulin molecule that comprises an antigen binding site of the required specificity.

Full length antibody molecules are comprised of two heavy chains (HC) and two light chains (LC) inter-connected by disulfide bonds as well as multimers thereof (e.g., IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The Vh and the VL regions may be further subdivided into regions of hyper variability, termed complementarity determining regions (CDR), interspersed with framework regions (FR). Each Vh and VL is composed of three CDRs and four FR segments, arranged from amino-to-carboxyl-terminus in the following order: FR1, CDR1, FR2, CDR2, FR3, CDR3 and FR4.

"Complementarity determining regions (CDR)" are "antigen binding sites" in an antibody. CDRs may be defined using various terms: (i) Complementarity Determining Regions (CDRs), three in the Vh (HCDR1, HCDR2, HCDR3) and three in the VL (LCDR1, LCDR2, LCDR3), are based on sequence variability (Wu et al. (1970) J Exp Med 132: 211-50 (Kabat et al., Sequences of Proteins of Immunological Interest, 5th Ed. Public Health Service, National Institutes of Health, Bethesda, Md., 1991). (ii) "Hypervariable regions," "HVR," or "HV," three in the Vh (H1, H2, H3) and three in the VL (L1, L2, L3), refer to the regions of antibody variable domains which are hypervariable in structure as defined by Chothia and Lesk (Chothia et al. (1987) J Mol Biol 196: 901-17. The International ImMunoGeneTics (IMGT) database (http://www_imgt_org) provides a standardized numbering and definition of antigen binding sites. The correspondence between CDRs, HVs and IMGT delineations is described in (Lefranc et al. (2003) Dev Comp Immunol 27: 55-77. The term "CDR," "HCDR1," "HCDR2," "HCDR3," "LCDR1," "LCDR2" and "LCDR3" as used herein includes CDRs defined by any of the methods described supra, Kabat, Chothia or IMGT, unless otherwise explicitly stated in the specification.

Conventional one and three-letter amino acid codes are used herein. Amino acid Three-letter code One-letter code:

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The polypeptides, nucleic acids, fusion proteins, and other compositions provided herein may encompass polypeptides, nucleic acids, fusion proteins, and the like that have a recited percent identity to an amino acid sequence or DNA sequence provided herein. The term "identity" refers to a relationship between the sequences of two or more polypeptide molecules or two or more nucleic acid molecules, as determined by aligning and comparing the sequences. "Percent identity," "percent homology," "sequence identity," or "sequence homology" and the like mean the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. In calculating percent identity, the sequences being compared are typically aligned in a way that gives the largest match between the sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage, and the like.

Furthermore, as used herein, a "polypeptide" refers to a protein that includes modifications, such as deletions, additions, and substitutions (e.g., conservative in nature as would be known to a person in the art) to the native sequence, as long as the protein maintains a desired activity. These modifications can be deliberate, as through site-directed mutagenesis, or can be accidental, such as through mutations of hosts that produce the proteins, or errors due to PCR amplification or other recombinant DNA methods.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules, cDNA, or a hybrid of these, single stranded or double stranded. The vector may be a bacterial phagemid and/or a plasmid. The vector may be an expression vector or a vector that enables a phage to display a protein of interest. For example, a pTavo phagemid/plasmid as disclosed herein can be a vector that comprises polynucleotides encoding a coat protein of a bacterial phage, or a vector that does not comprise polynucleotides encoding such a coat protein. See, e.g., FIG. 5 (B). The vector may comprise one or more tags, e.g., for purification and/or detection, e.g., by ELISA, BLI, and/or SPR. The one or more tags can be chosen from polyhistidine (HIS) and hemagglutinin (HA) tags. The tags can be fused with a VHO, and/or with the coat protein. See, e.g., FIG. 5 (A).

"Expression vector" refers to a vector that can be utilized in a biological system or in a reconstituted biological system to direct the translation of a polypeptide encoded by a polynucleotide sequence present in the expression vector.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

"Specific binding" or "specifically binds" or "binds" refer to an antibody binding to a specific antigen with greater affinity than for another antigen. Typically, the antibody "specifically binds" when the equilibrium dissociation constant (KD) for binding is about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with the KD that is at least one hundred-fold less than its KD for binding to a non-specific antigen (e.g., BSA, casein). The KD may be measured using standard procedures.

A "phage display library," as used herein, refers to a protein expression library, constructed in a bacteriophage, e.g., an M13-derived, vector, which is capable of expressing or expresses a collection of cloned protein sequences as fusions with a phage coat protein. Antibody phage display libraries, and methods of generating such libraries, are known in the art (see, for example, Famm et al., J. Mol. Biol. 376:926-931, 2008; Carmen and Jermutus, Brief Funct Genomic Proteomic 1(2):189-203, 2002; and U.S. Pat. Nos. 6,828,422 and 7,195,866). For example, a VHO phage display library as disclosed herein is capable of displaying or displays a library of VHO domains on a phage, e.g., an M13 phage.

"VHO," "VHO region," "VHO domain," or "VHO protein," as used herein, means a polypeptide that shares conserved sequences (protein or DNA), e.g., having at least 55%, 60%, 65%, 70%, 75%, 80%, 85%, 90%, 95%, 96%, 97%, 98%, or 99% sequence identity, with the Vh region of human, camel, and llama antibody Vh families, e.g., the human Vh region of the human antibody Vh3 family. Depending on the context, "VHO," "VHO region," or "VHO domain" may be used to refer to a polynucleotide sequence that encode the VHO polypeptide.

Leader Peptides

In certain embodiments, a leader peptide or leader sequence is chosen to drive the secretion of a VHO protein described in this disclosure into the cell culture supernatant as a secreted protein. Any leader peptide for any known secreted proteins/peptides can be used.

As used herein, a "leader peptide" or "signal peptide" includes a short peptide, usually 16-30 amino acids in length, which is present at the N-terminus of newly synthesized proteins that are destined towards the secretory pathway. Although leader peptides are extremely heterogeneous in sequence, and many prokaryotic and eukaryotic leader peptides are functionally interchangeable even between distinct species, the efficiency of protein secretion may be strongly determined by the sequence of the leader/signal peptide.

Linker Peptides

In some embodiments, there may be one or more linker peptides between the VHO, the coat protein, and the one or more tags. See, e.g., FIG. 5 (A). For example, there may be a linker peptide between the VHO and the one or more tags (e.g., Fc, HIS tag and/or HA tag). There may also be a linker peptide between VHO and the coat protein. In some embodiments, the linker peptide can be substituted by any other peptide that aids in the activities for displaying on phage or use of tags for purification or assay detection purposes.

Suitable linker peptides (also referred to as "spacers") can be readily selected, and can be of any of a number of suitable lengths, such as from 1 amino acid to 30 amino acids (e.g., any specific integer between 1 and 30, or from 1 amino acid (e.g., Gly) to about 20 amino acids (e.g., 2-15, 3-12, 4-10, 5-9, 6-8, or 7-8 amino acids).

Exemplary linker peptides include glycine polymers (G)n, glycine-serine polymers (including, for example, (GS)n, (GSGGS)n (SEQ ID NO: 13) and (GGGS)n (SEQ ID NO: 14), where n is an integer of at least one, e.g., 1, 2, 3, 4, 5, 6, 7, 8, 9, 10, 11, 12, 13, 14, 15, 16, 17, 18, 19, 20), glycine-alanine polymers, alanine-serine polymers, alanine-proline, immunoglobulin isotype and subtype hinge that can comprise IgG1, IgG2, IgG3, IgG4, IgA, IgE, IgM, and other flexible linker peptides known in the art. Both Gly and Ser are relatively unstructured, and therefore can serve as a neutral tether between components.

In certain embodiments, the linker peptide is a Glycine polymer. Glycine accesses significantly more phi-psi space than even alanine and is much less restricted than residues with longer side chains (see Scheraga, Rev. Computational Chem. 11173-142 (1992)). Exemplary linker peptides can comprise amino acid sequences including, but not limited to, GGS, GGSG (SEQ ID NO: 15), GGSGG (SEQ ID NO: 16), GGGGS (SEQ ID NO: 17), GSGSG (SEQ ID NO: 18), GSGGG (SEQ ID NO: 19), GGGSG (SEQ ID NO: 20), GSSSG (SEQ ID NO: 21), and the like.

In certain embodiments, the linker peptide is a rigid linker (Chen, Zaro et al. 2013). Exemplary rigid linker peptides can comprise amino acid sequences including, but not limited to, proline-rich sequence, (XP)n, with X designating any amino acid, preferably Ala, Lys, or Glu, where n is an integer of at least one, e.g., 1, 2, 3, 4, 5, 6, 7, 8, 9, 10, 11, 12, 13, 14, 15, 16, 17, 18, 19, 20. Exemplary rigid linker peptides can also comprise amino acid sequences including, but not limited to, alpha helix-forming linkers with the sequence of (EAAAK)n (SEQ ID NO: 22), where n is an integer of at least one, e.g., 1, 2, 3, 4, 5, 6, 7, 8, 9, 10, 11, 12, 13, 14, 15, 16, 17, 18, 19, 20.

Design, Synthesis, and Construction of VHO Libraries

Figure 2:
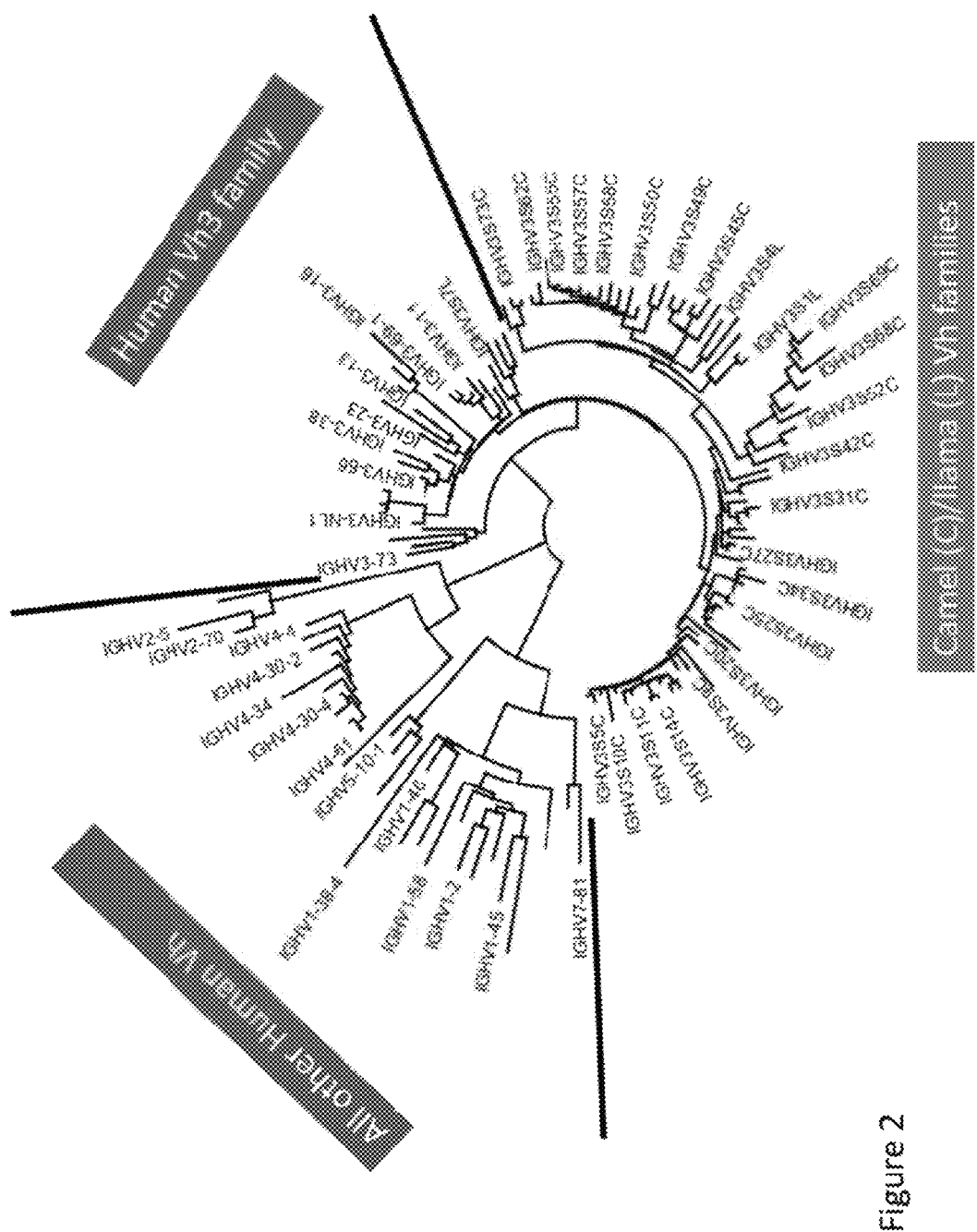
FIG. 2 shows a homology amino acid sequence alignment tree generated using the Geneious Prime software (https://www.geneious.com/prime/) using the amino acid sequences of the human, llama, and camel heavy V-region families from the IMGT.

The present disclosure provides a VHO platform to generate single domain-based therapeutic compounds. In one embodiment, the present disclosure provides a VHO library (also referred to herein as a TavoSelect library) based on the human variable domain of a human Vh family, such as the gene family Vh3. The Vh regions of the human antibody Vh3 family can be used as a scaffold for creating VHO libraries. For example, the human sequence IGHV3.23, a member of the IGVh3 family, can be used as a scaffold to construct a VHO library. The IGHV3 is selected because it has a more stable Vh than other human germline families (Ewert et al 2003). IGHV3 also has a high level of sequence identity to camel, llama, and alpaca IgG (see, e.g., FIGS. 2 and 3).

The VHOs described herein differ from other single domain antibodies (sdAb) and/or nanobodies (Nb) in that the VHOs comprise human amino acid sequences. Thus, there may be no need for any humanization methods for VHO panning as there is for camel, llama, and alpaca sdAb libraries.

In one embodiment, a VHO library is created in such a way that it captures the highest accuracy possible. "Accuracy" is defined as the absence of cysteine, methionine, and/or stop codons designed within the CDR regions of degeneracy as well as maintaining the open reading frame (ORF) from the initiating methionine codon to the designed stop codon.

In one embodiment, the present disclosure provides a VHO mutational library constituting a library of VHO polynucleotide sequences with variations (e.g., with randomized codons), wherein the VHO framework or scaffold is designed based on the Vh regions of the human Vh families, such as the Vh regions of the human Vh3 families.

The Vh3 family, based on IMGT nomenclature, may include the sub-family Vh3 members IGHV3-7, IVGH3-9, IVGH3-11, IVGH3-13, IVGH3-15, IVGH3-16, IVGH3-19, IVGH3-20, IVGH3-21, IVGH3-23, IVGH3-23D, IVGH3-25, IVGH3-30, IVGH3-30-3, IVGH3-30-5, IVGH3-33, IVGH3-35, IVGH3-38, IVGH3-43, IVGH3-47, IVGH3-48, IVGH3-49, IVGH3-52, IVGH3-53, IVGH3-64, IVGH3-66, IVGH3-69-1, IVGH3-72, IVGH3-73, and IVGH3-74.

In one embodiment, the present disclosure provides a VHO mutational library constituting a library of VHO polynucleotide sequences with variations (e.g., with randomized codons), wherein the VHO framework or scaffold is designed based on the Vh regions of IGHV3-23.

Figure 3:
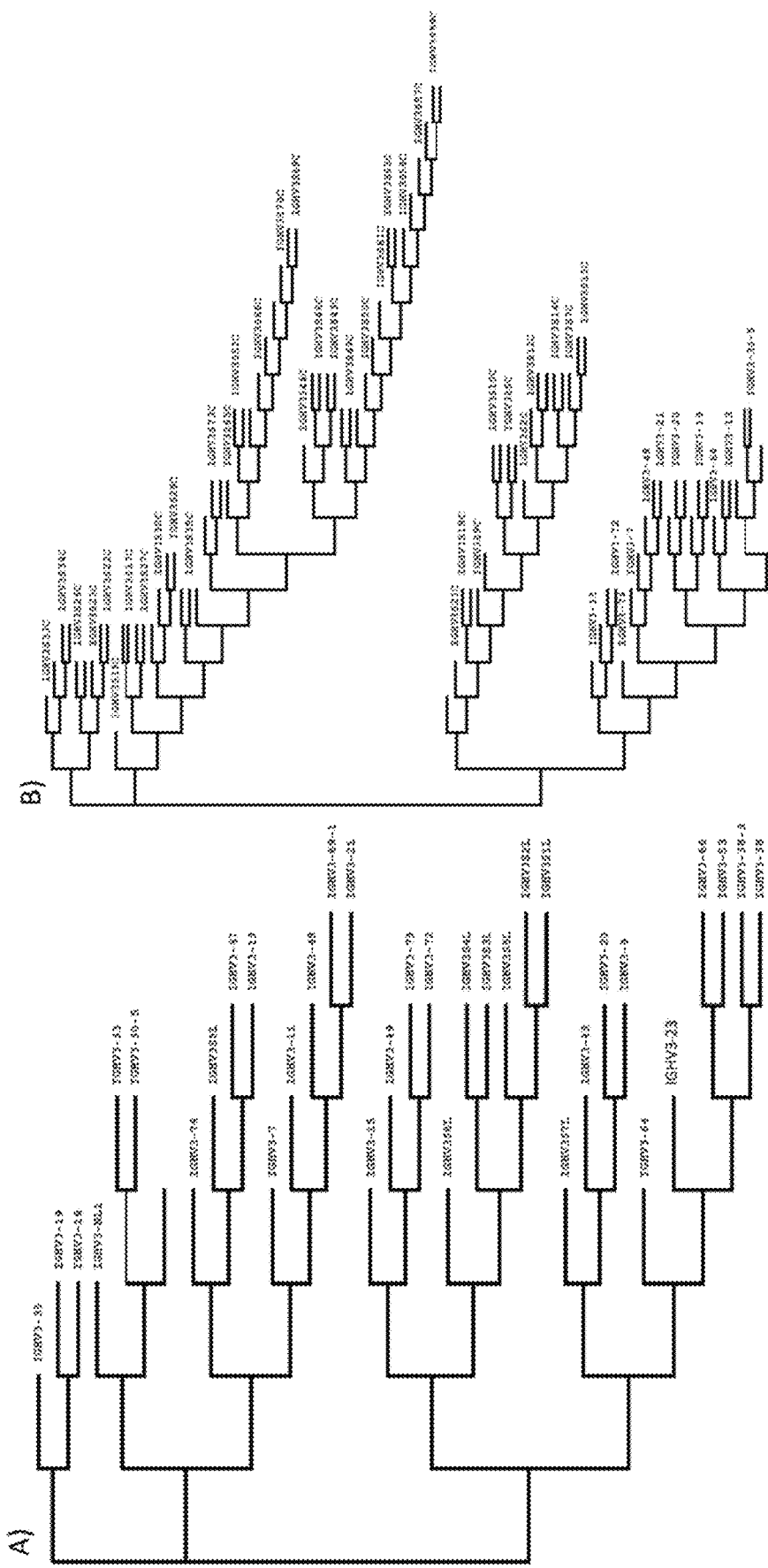
FIG. 3 shows homology amino acid sequence alignment trees generated using the Geneious Prime software (https://www.geneious.com/prime/).

In one embodiment, the present disclosure provides a VHO library based on human variable domain germlines that are homologous by amino acid sequence and/or similar in canonical structure to the Vh domains of a human Vh family. A canonical structure refers to the alignment of the CDR loops and the positioning of the sequences between the CDR loops. The human germline family Vh3 including all VDJ gene combinations defined by IMGT and/or other antibody resources are the closest in similarity to llama and camel VHHs including their VDJ gene combinations according to DNA and/or protein sequence BLAST search alignments based on the IMGT and/or any other antibody resource. FIG. 3 shows that the sequences of camel or llama VHH domains compared to human Vh domains have an average pairwise identity of 81% and 79% homology, respectively. The Vh3 germline family is most abundant in naïve and immunized humans (Herce, Schumacher et al. 2017). Vh3 germline family is more stable than other human heavy variable germline families (Ewert, Huber et al. 2003).

In one embodiment, a VHO library is created based on the consensus sequence of the fully human germline Vh3 family, e.g., generated by Geneious or other related software, by aligning all VDJ gene combinations as defined by the IMGT and/or other antibody resources. The alignment of the Vh3 family sequences can be based on the nucleotide or nucleic acid sequences (DNA alignment) or amino acid sequences (protein alignment). DNA sequences can also be generated corresponding to the aligned amino acid or residue type. Protein alignments can be performed applying the rules of canonical structures provided by resources like IMGT and the like.

In one embodiment, the present disclosure provides a VHO degenerate gene library of polynucleotides encoding various VHO (variable heavy only) domains, wherein the VHO domains have sequence homology and/or canonical loop region homology defined by IMGT with the Vh domain of a human Vh family, such as the Vh3 family, e.g., IGHV3-23. For example, the sequence homology (amino acids or nucleotides) is at least 60%, 65%, 70%, 75%, 80%, 85%, 90%, 95%, 98%, or 99%. The VHO domains can have residue diversity throughout the entire regions of the VHO domains. For example, the VHO domains have residue diversity in one or more of the CDR regions, e.g., in CDR1, CDR2, and/or CDR3 regions. For example, the VHO domains have residue diversity in one or more of the framework regions, e.g., in FR1, FR2, FR3, and/or FR4 regions. In one embodiment, the one or more of the framework regions can have one or more mutations that provide improvements in levels of protein expression, protein folding, protein purification, binding affinity, downstream target signaling, and/or inhibition of signaling. In one embodiment, the VHO domains have residue diversity in one or more of the CDR regions and in one or more of the framework regions. In one embodiment, the VHO domains have residue diversity in all of the CDR regions and in all of the framework regions. In one embodiment, the VHO comprises regions, e.g., CDR 1-3 and FR 1-4, typical of variable heavy chain domains according to IMGT or similar reference sources.

In one embodiment, a VHO library is designed to comprise gene modules that have CDR1 and CDR2 as one section and CDR3 as another section. The CDRs can also be designed to minimize aggregation by disrupting residues involved with the Vh and VL associations found in scFv, Fab, and IgG molecules. Using different residues at certain positions in the CDRs as well as the frameworks that normally provide Vh regions to interact with V1 regions, will reduce the VHO molecules from aggregating. Thus, the VHO library is different from the camel, llama, and alpaca VHH antibody libraries where aggregation arises from intermolecular sdAb interactions.

In one embodiment, the small paratopes of sdAbs derived from a VHO library disclosed herein will enable screening of many formats of biopanning of a given target antigen. This diverse biopanning approach along with the smaller paratopes of the VHOs enables many epitopes to be discovered on the target surface. Having more epitopes can improve the chance of finding superior therapeutic or diagnostic biologics molecules.

In one embodiment, the length of CDR3, defined by either IMGT, KABAT, CLOTHIA, or Martin definitions as well as combinations of such, can range from 1 to 30 amino acids, such as 6, 7, 8, 9, 10, 11, 12, 13, 14, 15, 16, 17, 18, 19, 20, 21, 22, 23, 24, 25, 26, 27, 28, 29, to 30 amino acids (6 to 30 codons of the corresponding polynucleotide sequence).

In one embodiment, a VHO library can include one or more sub libraries. For example, the length of CDR3 on the VHOs can be varied, thus multiple sub libraries within a VHO library can be created.

In one embodiment, the VHO framework or scaffold is designed based on the following consensus sequences, generated by Geneious or other related software uploaded with amino acid sequences from IMGT, of all VJ regions of human Vh families:

(SEQ ID NO: 5)
QVQLVESGGGLVKPGGSLRLSCAASGFTFS(X)WVRQAPGKGLEWV(X)D

SVKGRFTISRDNSKNTLYLQMNSLRAEDTAVYYCAR(X)WGQGTLVTVS

S.

In one embodiment, the VHO framework or scaffold is designed based on the following consensus sequences, generated by Geneious or other related software uploaded with amino acid sequences from IMGT, of all VJ regions of human Vh3 subfamilies:

(SEQ ID NO: 6)
EVQLVESGGGLVQPGGSLRLSCAASGFTFS(X)NWVRQAPGKGLEWV(X)

DSVKGRFTISRDNSKNTLYLQMNSLRAEDTAVYYCAR(X)WGQGTLVTVS

S.

Certain non-conserved positions in the CDR regions of a human variable heavy domain are marked by "X" in SEQ ID NOs: 5 and 6. The "X" is a symbol for degenerate mutagenesis of any kind applied to a codon that is translated into appropriate amino acid. The placement of "X" can be set at any defined CDR positions according to IMGT, KABAT, Clothia, or Martin definitions as well as combinations of such definitions for human variable regions. An "X" can be placed at any position within a variable heavy domain, such as SEQ ID NO: 5 and 6, and any combination of amino acid distribution or relative codon distribution can be used to replace X.

In one embodiment, a position denoted with "X" is replaced with an even distribution of all twenty naturally occurring amino acids except for C for CDR1, C and M for CDR2, and C, M, and N for CDR3. For example, "X" in CDR1 is not replaced by C (Cys) residue, "X" in CDR2 is not replaced by C or M residue, "X" in CDR3 is not replaced by C, M, or N residue. Any other combination of amino acids and distribution of each amino acid is deemed equal. Such distributions can be created by DNA degenerate synthesis methods/technologies such as NNK or TRIM (Ferreira Amaral, Frigotto et al. 2017) (Li A, Sun Z, Reetz M T. 2018) (Suchsland R, Appel B, Müller S. 2018).

Designs of degeneracy within the variable region can be determined as disclosed herein. Multiple standard methods to design mutations in the variable regions can also be used to create a more diverse library. Design of the VHO consensus scaffold and/or libraries of degeneracy can also consider factors such as translation of the VHO scaffold and/or libraries of degeneracy in bacterial (e.g., *Escherichia coli*), yeast, or mammalian (e.g., human or Chinese hamster ovary cells). For example, design of the VHO scaffold and/or libraries of degeneracy can consider combinations of codon usage or codon optimization typically designed by those skilled in the art.

In one embodiment, the polynucleotide sequences in a VHO library as disclosed herein are placed in a vector such as a bacterial phagemid and/or plasmid. In one embodiment, the vector contains one or more elements of function for controlled growth via antibiotic resistance, an Ori site for DNA replication, an Ori site for phage replication, promoter for driving protein expression, secretion signal (e.g., a leader sequence for driving secretion of translated proteins), and a repressor to control levels of protein expression as typically used by those skilled in the art. Depending on the host system used, certain combinations of the codon use and phagemid/plasmid elements can be used to obtain more efficient expression of the genes into proteins.

In one embodiment, a VHO library disclosed herein is placed into an expression cassette within a phagemid/plasmid, e.g., pTAVO as shown in FIG. 5(B).

In one embodiment, the present disclosure provides a phage library, wherein the VHO domains as described herein are capable of being displayed or are displayed on a viral particle produced by a prokaryotic or a eukaryotic cell, on a virus that infects a prokaryotic and/or eukaryotic host cell, or on a prokaryotic or a eukaryotic cell.

In one embodiment, the present disclosure provides a VHO library on a bacteriophage such as an M13 filamentous bacteriophage. Any coat protein of a bacteriophage, e.g., M13, can be connected by way of in-frame genetic fusion to either the amino or carboxyl terminal end of a VHO domain. For example, a VHO can be fused with any coat protein, e.g., PVII, PIX, PIII, and/or PVI, e.g., pVII and/or pIX, of an M13 filamentous bacteriophage. (See Høydahl, Nilssen et al. 2016) The fusion comprising a VHO and a coat protein can be further fused with other tag or tag combinations understood to those skilled in the art. FIG. 5(A) illustrates a schematic representation showing a VHO fused with a bacteriophage coat protein (e.g., VHO fused with coat protein pIX with a HIS tag and HA tag). FIG. 5(C) shows a schematic representation of a VHO fused to an M13 phage (displayed on an M13 phage).

Synthesis and construction of VHO mutational libraries can be conducted by methods understood by one skilled in the art. The VHO mutational libraries as disclosed herein can be placed in a phagemid/plasmid construct by cloning methods understood by one skilled in the art. For example, the NcoI and NotI restriction sites depict the area on pTAVO as to where the DNA of the VHO mutational libraries is inserted to obtain ligated VHO library constructs such as a VHO phage library. Furthermore, a combination of recombinant and restriction enzyme cloning methods can be used to construct the VHO mutational libraries within each cassette.

Transformation by VHO Phage Libraries

Ligated VHO phage library constructs can be transformed into cells, such as MC1061F' cells or equivalent strains (JM105, JM107, JM110, DH1, GM48, SL10, TD1, MC4100, SK1592, etc.) capable of being infected by M13 filamentous bacteriophage, as illustrated by exemplary embodiments below. Transformational efficiencies from $1 \times 10^6$ to $1 \times 10^{11}$ (colonies per amount of ligated DNA) can be obtained in a typical laboratory environment. Transformation efficiency is calculated by determining how many colony forming units (transformants) one can obtain from a reaction of one microgram of DNA.

Bacterial cultures can be transformed with a VHO phage library, e.g., a VHO library with a fixed CDR3 length. If a VHO phage library includes multiple sub libraries with different CDR3 lengths, multiple bacterial cultures can be transformed respectively with VHO sub-libraries of each CDR3 length.

Bacterial cultures transformed with a VHO phage library, e.g., a VHO sub-library with a fixed CDR3 length, are grown to log phase. The cultures are infected with a helper phage, such as a VCSM13 helper phage, and grown overnight under induction conditions. The overnight phage library amplification cultures undergo phage harvest methods. Titers of at least $1 \times 10^{12}$ colony-forming-units or plaque-forming-units are obtained. Rolling circle and Sanger sequencing methods are performed on single infected colonies. For example, the sequences obtained from sequencing of the single infected colonies are processed for translation and then aligned to one another as well as a VHO DNA sequence template (e.g., matching germline Vh sequence obtained from IMGT). This sequence analysis looks for in frame translation from the secretion signal to the expected final stop codon. In one embodiment, any sequence containing Cysteine, Methionine, or a stop codon located within one or more of the CDRs is not accepted as an accurate VHO. Typical accuracy of these VHO libraries range from 30-60%. FIG. 5 (C) portrays an example of how a VHO is displayed on the surface of an M13 phage through a genetic fusion with the minor coat protein pIX. Fab phage libraries having similar diversities, transformation efficiencies and functional accuracies gave rise to many successful biopanning projects (Shi et al, 2007).

Screening of VHO Phage Libraries

A VHO phage library as disclosed herein can be screened using panning (or biopanning) methods against a target as illustrated by the following exemplary embodiments. A target can be a protein, cell, tissue, or combinations thereof. For example, a VHO pIX phage display library is added to a target for screening. This allows for binding to occur between the VHO parts of the phage library and the target. To capture target specific VHOs, non-specifically bound VHO pIX phages are washed away. The VHO-phages still bound to the target after washing are captured by either using an acid or just applying bacteria cells for direct infection. For example, the infected bacteria carrying the VHO candidates are expanded in culture usually within 4 hours. Once the expanded culture is at optimal cell density (e.g., OD600 nm=0.6-0.8), helper phage is added to the culture so that the amount of plaque forming units (pfu) reaches at least 10× greater than the number of cells. The helper phage infected bacteria cells are induced for expression of the selected VHO candidates fused to the phage and the culture is incubated overnight. This stage is called phage amplification, which can be performed after each round of biopanning known by those skilled in the art. For example, the bacterial cells cultures carrying the VHO candidates can be incubated for 8-16 hours.

The steps for biopanning can be repeated for multiple times, such as at least three times, 4 times, or 5 times. Efficacy as to whether biopanning is working is determined by how dense the cultures have grown between each round of biopanning since they are under antibiotic pressure. The culture from the final round of biopanning is used to capture the phagemid DNA sequences encoding the selected VHO candidates from the biopanning process, e.g., those VHO candidates that are capable of binding to a target after the biopanning process. The captured phagemid DNA sequences are used to generate NGS libraries (Suckling, McFarlane et al. 2019) (Head, Komori et al. 2014) so as to sequence each VHO candidate (Dias-Neto, Nunes et al. 2009). Each panning group, e.g., a panning group that screens a given target, (for instance a panning group focused on human TNF, a panning group focused on cynomolgus TNF, or a panning group focused on mouse TNF), makes up its own NGS amplicon library.

Figure 6:
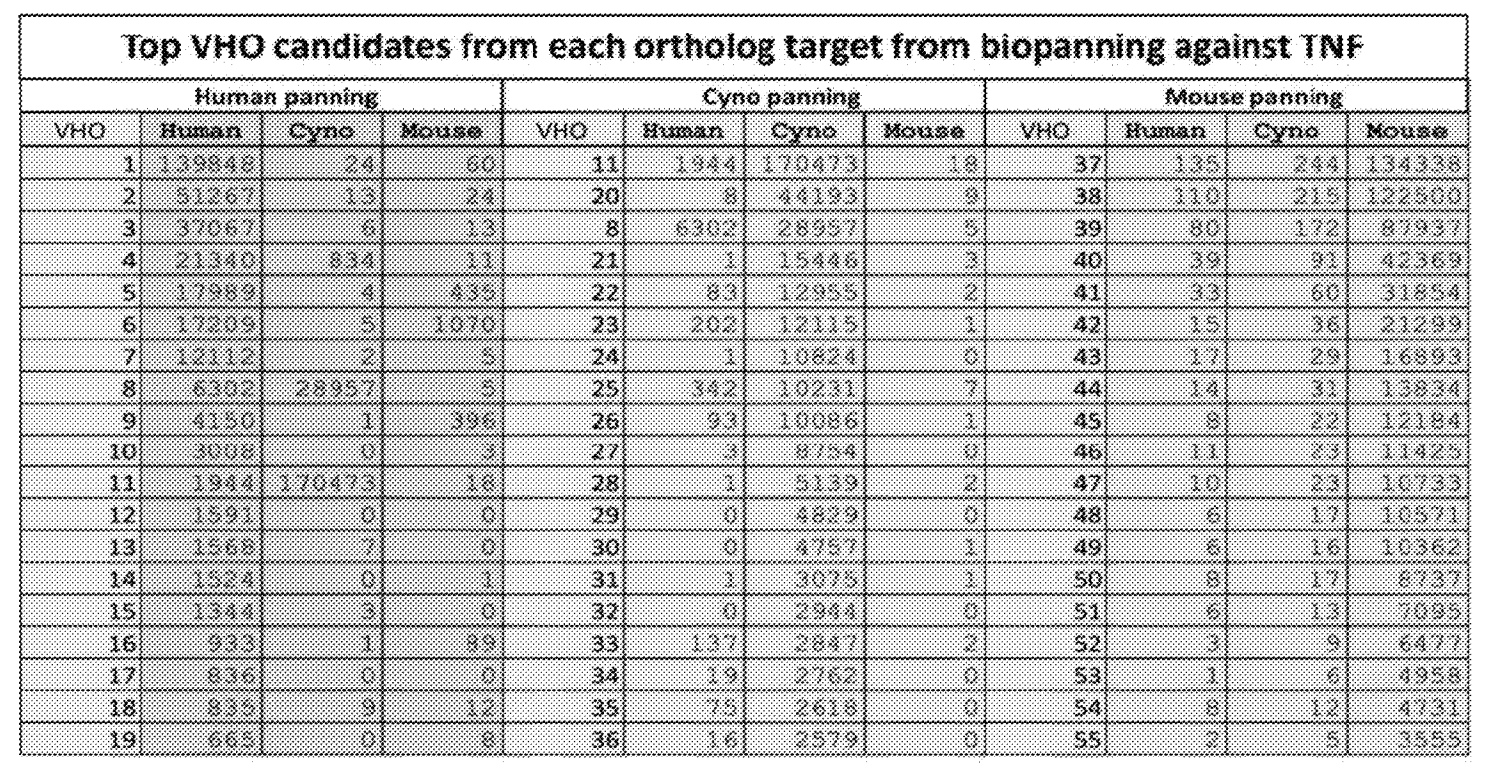

For example, primer-based indices Nextera-XT (www.illumina.com) are applied in such a way to later distinguish from which panning group each sequence is selected. The PCR and bead-based purification steps needed to create these indexed amplicon libraries are created based on (16S Metagenomic Sequencing Library Preparation, Illumina part #15044223 Rev B. https://support.illumina.com/documents/documentation/chemistry_documentation/16s/16 s-metagenomic-library-prep-guide-15044223-b.pdf) using 30 ng of panning output DNA and 16S primers diluted to 0.1 µM with gene specific sequence priming sites. Specifically, the forward primer has a TM of 62.6° C. and the reverse primer has a TM of 61.3° C. Both primers are designed to anneal on flanking areas to capture the CDR diversity of the selected VHOs from the biopanning process. The final NGS amplicon library product contains an approximate range of 250-300 bp length region making up of heavy chain CDR1 through heavy chain CDR3. These amplicon libraries are applied to a 2×300 paired MiSeq run. Obtained from such a MiSeq run is 20-25 million sequences. These sequences are organized by quality scores (Fastq) and separated by biopanning indices utilizing BaseSpace software (Illumina). The data is delivered in unpaired Fastq format separated according to the indices that define each biopanning group. Processing applications organizes up to twenty-five million sequences down to 1000 to 100,000 unique protein sequences per MiSeq run which can further be extrapolated based on indices/biopanning groups as disclosed herein.
Determination of Specificity of Selected VHO Candidates As an illustrative embodiment, sequence results from NGS are grouped according to the targets used in the biopanning or the environment used in biopanning. For example, the target proteins used can be from three distinct species: human, cynomolgus monkey (cyno), and mouse. The ECD (extracellular domain) of human TNF shows 97% and 79% identity with the ECD of cyno and mouse TNF, respectively. DNA isolated from each biopanning group, for example, against human, cyno, and mouse TNF, respectively, is used for creating NGS libraries where each group is "indexed" (Head, Komori et al. 2014) (Li, Zhao et al. 2019) to aid in the specific recovery of VHO candidate sequences. Initially millions of sequences are processed into each indexed biopanning group. Within each biopanning group there is a sequence distribution of all the selected VHO candidates. After the DNA sequences of the selected VHO candidates are processed into peptide sequences, distinct sequences for a particular panning of the VHO candidates can be determined. For example, specificities such as sequences only found within a biopanning group and sequences found in more than one biopanning group are picked for further assessment. A list of candidate sequences from three biopanning groups, i.e., against human, cyno, and mouse TNF, respectively, for further assessment is shown in FIG. 6.

The VHO candidates determined from the NGS processing are picked for either clonal soluble VHO expression or displayed on phage to be assessed for binding specificity to the same respective targets used in the biopanning process. For example, certain expressed VHO candidates (e.g., with a tag such as HIS or Fc) are applied as analytes in biolayer interferometry (BLI) kinetics assay. FIG. 7 shows binding activities of a set of VHO-Fc fusions (VHO3-Fc, VHO4-Fc, and VHO5-Fc, comprising VHO sequences set forth in SEQ ID NOs: 7, 8, and 9, respectively) in BLI experiments (GatorBio) to two distinct species (human and mouse FCRN proteins) and two different pH specificities (pH 6 and pH 7).

```
                                            (SEQ ID NO: 7)
EVQLLESGGGLVQPGGSLRLSCAASGFTFSTYWMSWVRQAPGKGLEWVSV

ISGDGGSTYYADSVKGRFTISRDNSKNTLYLQMNSLRAEDTAVYYCAKWK

GAGRGPGALGGLDVWGQGTLVTVSS.

(SEQ ID NO: 8)
EVQLLESGGGLVQPGGSLRLSCAASGFTFSSYGMSWVRQAPGKGLEWVSA

IWSDGSSTYYADSVKGRFTISRDNSKNTLYLQMNSLRAEDTAVYYCARRT

WGHQFDYWGQGTLVTVSS.

(SEQ ID NO: 9)
EVQLLESGGGLVQPGGSLRLSCAASGFTFSSYWMHWVRQAPGKGLEWVSV

INYSGSSTYYADSVKGRFTISRDNSKNTLYLQMNSLRAEDTAVYYCAMGT

PGELPLDYWGQGTLVTVSS.
```

The biopanning, NGS, and binding assay results show whether a VHO, e.g., a fully human VHO, binds to a target. The VHOs can be displayed on a pIX phage both in a diverse library setting and in the clonal phage stage. The example associated with FIG. 7 demonstrates that VHO phage display can be used to generate cross reactive VHO candidates to a target. The panning and NGS analysis methods can identify many VHO candidate sequences. More than one VHO candidate shows correlation between the biopanning and NGS analysis and with the specificity binding results in BLI. The data in FIG. 7 further shows diverse binding activities of the VHOs. For example, the different curves in steps 3 and 4 of the BLI runs are indicative of the diverse binding activities with the use of two orthologs of the target and two pH values used.

Figure 8:
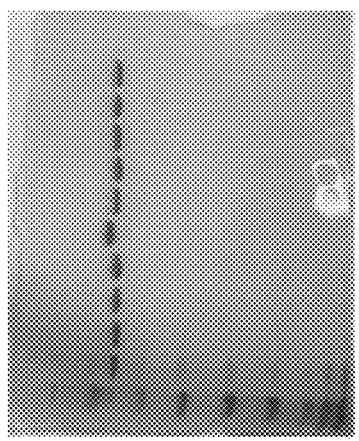
FIG. 8A shows examples of size exclusion chromatography results of two different VHO-Fc molecules (VHO1-Fc comprising SEQ ID NO: 10; VHO2-Fc comprising SEQ ID NO: 11) compared to a human IgG1 molecule. The results confirm the presence of monodisperse VHO-Fc fusion proteins.
FIG. 8B shows an example of the purity of VHO-Fc proteins (Non reduced VHO-Fc fusion candidates after a magnetic bead-based purification) on non-reduced SDS-PAGE.
Figure 10:
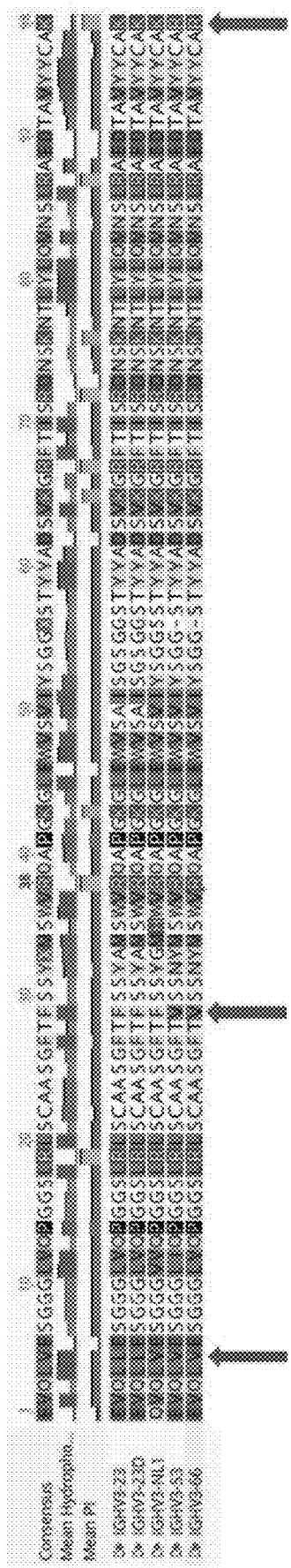
FIG. 10 shows an alignment of the closest human variable heavy domains to the germline sub-family member (IGHV3-23). IGHV3-23 was used as the scaffold to build the VHO phage libraries in some embodiments of this disclosure. Recently, Wu et al (2020) describes generating an sdAb phage library using the germline family IGHV3-66. The arrows point out some framework differences between IGHV3-66 and IGHV3-23.

FIG. 8 shows how well behaved (e.g., no severe aggregation) a VHO can be, compared to the other proteins, such as IgGs. For example, after completing 217 transiently expressed candidates of VHO-Fc fusion proteins, no aggregation was observed with the VHO-Fc fusions. Of the 217 candidates, 88% expressed as VHO-Fc dimers had bands that corresponded to the MW predicted based on the sequences by non-reducing SDS-PAGE (see examples illustrated in FIG. 8B). FIG. 8A shows examples of size exclusion chromatography results of two different VHO-Fc molecules (denoted as "VHO1-Fc" and "VHO2-Fc") compared to a human IgG1 molecule. The size exclusion chromatography chromatograms of FIG. 8A are typical of VHO-Fc proteins disclosed herein. The single peak profiles on the chromatogram of FIG. 8A indicate presence of the VHO proteins with the correct molecular weight with minimal aggregation or clipping.

"VHO1-Fc" and "VHO2-Fc," characterized in FIG. 8A, comprise the following VHO sequences, respectively.

(SEQ ID NO: 10)
EVQLLESGGGLVQPGGSLRLSCAASGFTFSDYGMHWVRQAPGKGLEWVSG

ISYSGSSTYYADSVKGRFTISRDNSKNTLYLQMNSLRAEDTAVYYCARPR

WAVPGRGHPRFDYWGQGTLVTVSS.

(SEQ ID NO: 11)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSS

FDYWGQGTLVTVSS.

EXAMPLES

Example 1. Library Construction

An initial cassette containing pIX, HIS, and HA tags without the VHO gene was cloned into pTAVO by using NcoI and NotI restriction enzyme sites. FIG. 5(B) illustrates pTAVO with the NcoI and NotI restriction enzyme sites. CDR1 and CDR2 diversity as DNA fragments synthesized by a CRO were cloned into the pTAVO, which already contains pIX, HIS, and HA tags, by using restriction enzymes such as PstI and NcoI according to appropriate digest parameters. The pTAVO already containing CDR1 and CDR2 diversity, as well as pIX, HIS, and HA tags, was amplified and then used as a partial library containing vector to insert the more diverse CDR3 region library using restriction enzymes such as PstI and XhoI. T4 ligase was used in all cloning steps after gel extraction of vectors and DNA fragments, following the recommended methods from vendors. The amount of digested CDR1 and CDR2 or CDR3 fragments and digested pTAVO or partial library pTAVO vectors are placed in an T4 ligase reaction set at a molar ratio of at least 2:1 but not limited to this ratio, respectively. Ligated libraries, e.g., pTAVO containing CDR1, CDR2, and CDR3 diversity, as well as pIX, HIS, and HA tags, were cleaned up in a way to avoid DNA loss, for example by glycogen and butanol precipitation. The ligated libraries at 500-1000 ng of DNA were mixed into 5-10 aliquots of competent MC1061 F' *E. coli* each set at $10^8$ cells per aliquot. The DNA/cell mixture underwent electroporation following optimized parameters for highest transformation efficiencies. The transformed cells were allowed to recover from antibiotic resistance, grown to log phase, and then infected with M13 helper phage. The infected cells with the ligated libraries were grown under optimal phage and VHO protein expression conditions for 16-18 hours. The VHO library phages were precipitated and concentrated 10-fold and stored at −80° C. for use in subsequent biopanning. The culture media used for all bacteria/phage library conditions was 2×YT. Glucose was used to repress VHO expression prior to phage amplification using a Lac repressor. VHO and phage expression were induced by 1 mM IPTG with a Lac promoter without glucose.

Example 2. Phage Biopanning

Phage libraries and streptavidin (SA) linked magnetic beads (Life Technologies, M280 streptavidin ferrous based beads) were pre-loaded with biotinylated target antigens, e.g., human, mouse, or cynomolgus TNF orthologs. A magnetic separator was used to effectively separate the beads from solutions during certain steps of the biopanning experiment, e.g., tubes were placed in a magnetic separator during the washing steps so as to rid non-specific bound phage from the specifically bound phage on the beads. The target bound SA beads were blocked with agents such as milk or Chemiblocker to reduce non-specific binding by the VHO phage libraries. Nonspecific (e.g., non-binding to the target-loaded beads) VHO phages were removed by washing with buffer such as PBS. Log phase MC1061 F' *E. coli* cells were used to capture (infect) those phages that retain the preferred biopanned characteristics, capable of binding to the target-loaded beads during the last round of biopanning. After amplification of the captured VHO phages and subsequent rounds of biopanning, the final round of target specific VHO phages captured by log phase MC1061 F' by infection was grown overnight under suppression conditions of expression. DNA preparations on this final culture of biopanned output was performed following vendor's protocol.

Example 3. NGS Analysis of Biopanned VHO Candidates

Based on the protocol outlined in the 16S Metagenomic Sequencing Library Preparation, Illumina part #15044223 Rev B. documentation (https://support.illumina.com/documents/documentation/chemistry_documentation/16s/16s-metagenomic-library-prep-guide-15044223-b.pdf), the following methods were used to create gene specific NGS amplicon libraries. The final round of biopanning output DNA was amplified using gene specific forward and reverse primers, which include the Illumina overhang adapter sequence. PCR was used to perform 25 cycles of amplification using KAPA HiFi Hot Start polymerase, and AMPure XP bead-based PCR cleanup was performed on the PCR reaction according to the protocol referenced above. DNA from the purified PCR reaction was used in a second PCR (index PCR) with 8 cycles of amplification using KAPA HiFi Hot Start polymerase and AMPure XP bead-based PCR cleanup. The samples were then normalized, denatured, mixed with denatured PhiX control, and loaded onto a single MiSeq run (Ravi R K, Walton K, Khosroheidari M. 2018) to determine the sequences of the VHO candidates.

Example 4. VHO Protein Production

VHO sequences established from biopanning and NGS were synthesized and cloned into a mammalian expression vector as Fc fusions (Lo et al, 1998). Each VHO-Fc construct was transiently expressed in HEK293 Expi cells (Invitrogen). The spent media from a 5-day culture was processed using a Protein A or Protein G methodology to purify the VHO-Fc protein (Fishman and Berg, 2019).

Example 5. VHO Protein Analysis

VHO-Fc proteins were assessed for yield, purity, and biologic activity. The yield was determined by absorbance at 280 nm using a spectrophotometer. The purity was assessed by SDS-PAGE and the monodispersity was confirmed using size exclusion chromatography. The biologic activity was measured by binding to the target protein or to cells with such target on its surface. Binding to a protein target can be done either by ELISA, biolayer interferometry, or any equivalent technique for protein-protein interactions. Binding activity was also measured on cells via flow cytometry.

Example 6. Epitope Screening

A library using a small part of an antibody, the variable heavy region, was designed. This small part allows for more epitopes to be covered on a given target. The VHOs are modularized to capture assorted designs of CDR diversity to increase the ability to capture more paratopes. Diverse methods of biopanning also improves on generating many epitopes and paratopes. NGS and sequence analysis methods help prioritize which selected VHOs to express as soluble proteins for downstream activity assessments.

FIG. 9 shows that the percentages of epitopes per candidate screened or characterized are higher for the VHOs according to the present disclosure, compared to traditional pannings of sdAb, Nb, and VHH. Researchers at Ablynx N.V. conducted a phage display effort against a single target and were able to get 3-4 epitopes from 96 candidates. (doi:10.3389/fimmu.2017.00420). Thus, the Ablynx study resulted in a successful target efficiency of 0.04 or 4% (4 epitope/96 candidates) (doi:10.3389/fimmu.2017.00420). Another group immunized phage display against 5 targets yielding a range of 3-6 epitopes from a range of 160-182 candidates. Their successful target efficiency was of 0.03 or 3% (30 epitopes from 867 candidates) (DOI: 10.7554/eLife.48750.009).

A VHO (fully synthetic and fully human) phage display library was used to pan 5 distinct targets. A total of 31 epitopes to 190 VHO candidates was obtained, resulting in a successful target efficiency of 0.16 or 16% (31 epitopes from 190 candidates) as shown in FIG. 9. Thus, a VHO library according to the present disclosure had a successful target efficiency larger than those in the art, which achieved successful target efficiencies of less than 5%.

The VHO molecules were expressed in mammalian cells as VHO-alone proteins and as Fc fusion proteins. The successful targeting VHO hit molecules in either format also had better expression behavior, monodisperse profiles as shown in FIG. 8, as well as binding activity as shown in FIG. 7.

Further exemplary embodiments are illustrated below.

1. A VHO library of polynucleotides encoding VHO (variable heavy only) domains, wherein the VHO domains have sequence homology and/or canonical homology with the Vh domain of a human Vh family.
2. The VHO library of embodiment 1, wherein the human Vh family is a human Vh3 family, e.g., IGHV3-23.
3. The VHO library of any of embodiments 1-2, wherein the sequence homology is at least 75%.
4. The VHO library of any of embodiments 1-3, wherein the VHO domains have residue diversity throughout the entire regions of the VHO domains.
5. The VHO library of any of embodiments 1-4, wherein the VHO domains have residue diversity in one or more of the CDR regions.
6. The VHO library of any of embodiments 1-5, wherein the VHO domains comprise SEQ ID NO: 5: QVQLVESGGGLVKPGGSLRLSCAASGFTFS(X) WVRQAPGKGLEWV(X)D SVKGRFTIS-RDNSKNTLYLQMNSLRAEDTAVYYCAR(X) WGQGTLVTVSS (SEQ ID NO: 5), wherein position X represents any one of the 20 naturally occurring amino acid residues.
7. The VHO library of any of embodiments 1-5, wherein the VHO domains comprise SEQ ID NO: 6:

```
                                        (SEQ ID NO: 6)
EVQLVESGGGLVQPGGSLRLSCAASGFTFS(X)NWVRQAPGKGLEWV(X)

DSVKGRFTISRDNSKNTLYLQMNSLRAEDTAVYYCAR(X)WGQGTLVTVS

S,
``` wherein position X represents any one of the 20 naturally occurring amino acid residues.

8. The VHO library of any of embodiments 6 and 7, wherein position X is replaced with an even distribution of all 20 naturally occurring amino acids except for C for CDR1, C and M for CDR2, and C, M, and N for CDR3.
9. The VHO library of any of embodiments 1-8, wherein the VHO domains have residue diversity in one or more of the framework regions.
10. The VHO library of any of embodiments 1-9, wherein one or more of the framework regions have one or more mutations that provide improvements in levels of protein expression, protein folding, protein purification, binding affinity, downstream target signaling, and/or inhibition of signaling.
11. The VHO library of any of embodiments 1-10, wherein the VHO domains have residue diversity in one or more of the framework regions and in one or more of the CDR regions.
12. The VHO library of any of embodiments 1-11, wherein the VHO domains have length diversity in the CDR3 region.
13. The VHO library of any of embodiments 1-11, wherein the length diversity of the CDR3 region ranges from 6 to 30 codons.
14. The VHO library of any of embodiments 1-13, wherein the polynucleotides encoding VHO domains are inserted into a vector.
15. The VHO library of any of embodiments 14, wherein the vector is a phagemid.
16. The VHO library of any of embodiments 14, wherein the vector is a plasmid.
17. The VHO library of any of embodiments 14-15, wherein the vector comprises polynucleotides encoding a coat protein of a bacterial phage.
18. The VHO library of embodiment 17, wherein the bacterial phage is M13 bacteriophage.
19. The VHO library of any of embodiments 17-18, wherein the coat protein is a pVII or pIX coat protein.
20. The VHO library of any of embodiments 14-19, wherein the vector comprises one or more tags.
21. The VHO library of embodiment 20, wherein the one or more tags are chosen from polyhistidine (HIS) and hemagglutinin (HA) tags.

22. The VHO library of embodiment 21, wherein the vector comprises a polynucleotide sequence encoding a linker peptide between the VHO and the one or more tags.
23. The VHO library of embodiment 21, wherein the vector comprises a polynucleotide sequence encoding a linker peptide between VHO and the coat protein.
24. The VHO library of any of embodiments 22-23, wherein the linker peptide is GGGGS (SEQ ID NO: 17).
25. The VHO library of any of embodiments 14-15 and 17-24, wherein the vector comprises elements that are arranged in a manner to allow for the VHO domains to be displayed on a bacteriophage.
26. The VHO library of any of embodiments 14-25, wherein the vector comprises elements that are arranged in a manner to allow for the VHO domains to be expressed.
27. The VHO library of any of embodiments 14, 16, 20-22, 24, and 26, wherein the vector comprises elements that are arranged in a manner to allow for the VHO domains to be expressed without a bacterial phage.
28. The VHO library of any of embodiments 14-27, wherein the vector has Ori site for DNA replication, an Ori site for phage replication, a leader sequence for driving secretion of translated proteins, a promoter for driving protein expression, and a repressor to control levels of protein expression.
29. The vector of any one of embodiments 14-28, wherein the vector comprises polynucleotides encoding any one of the VHO domains.
30. A phage library displaying the VHO domains encoded by the VHO library of embodiments 1-28.
31. The phage library of embodiment 30, wherein the VHO domains are displayed on a viral particle produced by a prokaryotic or a eukaryotic cell, displayed on a virus that infects a prokaryotic and/or eukaryotic host cell, or displayed on a prokaryotic or a eukaryotic cell.
32. A method of preparing the VHO library of any one of embodiments 1-28, comprising: providing polynucleotide sequences encoding the VHO domains of any one of embodiments 1-13; and inserting the polynucleotide sequences into the vector of any one of 14-29.
33. A method of preparing the phage library of any one of embodiments 30-31, comprising: transforming a bacterial cell culture with the VHO library of any one of embodiments 1-28,
allowing the bacterial cell culture to grow to a log phase, infecting the bacterial cell culture with a helper phage, and
amplifying the bacterial cell culture.
34. A method of identifying a VHO domain of interest that is capable of binding a target, comprising: creating a VHO library according to embodiment 32, creating a phage library of according to embodiment 33, and screening the phage library using biopanning against the target to identify the VHO of interest.
35. The method of embodiment 34, wherein the biopanning step is conducted multiple times.
36. The method of any one of embodiments 34-35, further comprising sequencing the VHO of interest by NGS.
37. The method of any one of embodiments 34-36, further comprising evaluating the binding affinity of the VHO of interest to the target.
38. The method of embodiment 37, wherein the binding affinity is evaluated using ELISA.
39. A VHO of interest identified by the method of any one of embodiments 34-38.
40. A polypeptide comprising the VHO of embodiment 39, wherein the VHO is fused to a protein chosen from immunoglobulins, receptors, cell surface proteins, and fragments thereof.
41. A composition comprising the VHO of embodiment 39 or the polypeptide of embodiment 40.
42. A polynucleotide that encodes the VHO of interest of embodiment 39 or the polypeptide of embodiment 40.
43. A polypeptide that has greater than 50% identity to the VHO of interest of embodiment 39.
44. A polynucleotide that encodes a protein that has greater than 50% identity to the VHO of interest of embodiment 39.
45. A vector comprising the polynucleotides of any one of embodiments 42 and 44.
46. A cell comprising the vector of embodiment 29.
47. A cell comprising the vector of embodiment 45.
48. A polypeptide comprising the VHO of embodiment 39, wherein the VHO is genetically fused to any tag, e.g., Fc domain of an immunoglobulin family of any species, poly histidine tag, and FLAG tag.
49. A polypeptide comprising the VHO of embodiment 39, wherein the polypeptide is expressed in mammalian cells.

REFERENCES

Li A, Sun Z, Reetz M T. Solid-Phase Gene Synthesis for Mutant Library Construction: The Future of Directed Evolution? Chembiochem. 2018 Oct. 4; 19(19):2023-2032.
Suchsland R, Appel B, Müller S. Preparation of trinucleotide phosphoramidites as synthons for the synthesis of gene libraries. Beilstein J Org Chem. 2018; 14:397-406.
Ravi R K, Walton K, Khosroheidari M. MiSeq: A Next Generation Sequencing Platform for Genomic Analysis. Methods Mol Biol. 2018; 1706:223-232. (2012).
3—Antibody structure-function relationships. Therapeutic Antibody Engineering. W. R. Strohl and L. M. Strohl, Woodhead Publishing: 37-595.
Aburatani, T., Ueda, H., Nagamune, T., (2002) Importance of a CDR H3 Basal Residue in VH/VL Interaction of Human Antibodies, J. Biochem., 132, 775-782.
Acevedo-Rocha, C. G., M. Ferla and M. T. Reetz (2018). "Directed Evolution of Proteins Based on Mutational Scanning." Methods Mol Biol 1685: 87-128.
Alt, F. W, Honjo, T, Radbruch A. and Reth, M. (Eds.), Molecular Biology of B cells, Second edition, Academic Press, Elsevier Ltd, London, UK, Chapter 26, 2014, PP. 481-514. dx.doi.org, ISBN: 978-0-12-397933-9. LIGM: 438 page 507-508
Arbabi-Ghahroudi, M. (2017). "Camelid Single-Domain Antibodies: Historical Perspective and Future Outlook." Frontiers in immunology 8: 1589-1589.
Belanger, K., U. Iqbal, J. Tanha, R. MacKenzie, M. Moreno and D. Stanimirovic (2019). "Single-Domain Antibodies as Therapeutic and Imaging Agents for the Treatment of CNS Diseases." Antibodies (Basel) 8(2).
Bruce, V. J., M. Lopez-Islas, and B. R. McNaughton (2016). "Resurfaced cell-penetrating nanobodies: A potentially general scaffold for intracellularly targeted protein discovery." Protein Sci 25(6): 1129-1137.

Dias-Neto, E., D. N. Nunes, R. J. Giordano, J. Sun, G. H. Botz, K. Yang, J. C. Setubal, R. Pasqualini and W. Arap (2009). "Next-generation phage display: integrating and comparing available molecular tools to enable cost-effective high-throughput analysis." PLoS One 4(12): e8338.

Ewert, S., C. Cambillau, K. Conrath and A. Plückthun (2002). "Biophysical properties of camelid V(HH) domains compared to those of human V(H)3 domains." Biochemistry 41(11): 3628-3636.

Ewert, S., T. Huber, A. Honegger, and A. Plückthun (2003). "Biophysical properties of human antibody variable domains." J Mol Biol 325(3): 531-553.

Ferreira Amaral, M. M., L. Frigotto and A. V. Hine (2017). "Beyond the Natural Proteome: Nondegenerate Saturation Mutagenesis-Methodologies and Advantages." Methods Enzymol 585: 111-133.

Fishman J B, Berg E A. Protein A and Protein G Purification of Antibodies. Cold Spring Harb Protoc. 2019 Jan. 2; 2019(1)

Gomes, J. R., I. Cabrito, H. R. Soares, S. Costelha, A. Teixeira, A. Wittelsberger, C. Stortelers, P. Vanlandschoot and M. J. Saraiva (2018). "Delivery of an anti-transthyretin Nanobody to the brain through intranasal administration reveals transthyretin expression and secretion by motor neurons." J Neurochem 145(5): 393-408.

Hamers-Casterman, C., Atarhouch, T., Muyldermans, S., Robinson, G., Hamers, C., Bajyana Songa, E., Bendahman, N., and Hamers, R. (1993). Naturally occurring antibodies devoid of light chains. Nature 363, 446-448.

Harmsen, M. M. and H. J. De Haard (2007). "Properties, production, and applications of camelid single-domain antibody fragments." Appl Microbiol Biotechnol 77(1): 13-22.

Head, S. R., H. K. Komori, S. A. LaMere, T. Whisenant, F. Van Nieuwerburgh, D. R. Salomon, and P. Ordoukhanian (2014). "Library construction for next-generation sequencing: overviews and challenges." Biotechniques 56(2): 61-64, 66, 68, passim.

Herce, H. D., D. Schumacher, A. F. L. Schneider, A. K. Ludwig, F. A. Mann, M. Fillies, M. A. Kasper, S. Reinke, E. Krause, H. Leonhardt, M. C. Cardoso and C. P. R. Hackenberger (2017). "Cell-permeable nanobodies for targeted immunolabelling and antigen manipulation in living cells." Nat Chem 9(8): 762-771.

Herold, E. M., C. John, B. Weber, S. Kremser, J. Eras, C. Berner, S. Deubler, M. Zacharias and J. Buchner (2017). "Determinants of the assembly and function of antibody variable domains." Sci Rep 7(1): 12276.

Høydahl, L. S., N. R. Nilssen, K. S. Gunnarsen, M. F. d. Pre, R. Iversen, N. Roos, X. Chen, T. E. Michaelsen, L. M. Sollid, I. Sandlie and G. Å. Løset (2016). "Multivalent pIX phage display selects for distinct and improved antibody properties." Scientific Reports 6(1): 39066.

Joyce, C., D. R. Burton, and B. Briney (2020). "Comparisons of the antibody repertoires of a humanized rodent and humans by high throughput sequencing." Sci Rep 10(1): 1120.

Li, Q., X. Zhao, W. Zhang, L. Wang, J. Wang, D. Xu, Z. Mei, Q. Liu, S. Du, Z. Li, X. Liang, X. Wang, H. Wei, P. Liu, J. Zou, H. Shen, A. Chen, S. Drmanac, J. S. Liu, L. Li, H. Jiang, Y. Zhang, J. Wang, H. Yang, X. Xu, R. Drmanac and Y. Jiang (2019). "Reliable multiplex sequencing with rare index mis-assignment on DNB-based NGS platform." BMC Genomics 20(1): 215.

Li, T., J. P. Bourgeois, S. Celli, F. Glacial, A. M. Le Sourd, S. Mecheri, B. Weksler, I. Romero, P. O. Couraud, F. Rougeon and P. Lafaye (2012). "Cell-penetrating anti-GFAP VHH and corresponding fluorescent fusion protein VHH-GFP spontaneously cross the blood-brain barrier and specifically recognize astrocytes: application to brain imaging." FASEB J 26(10): 3969-3979.

K M Lo, Y Sudo, J Chen, Y Li, Y Lan, S M Kong, L Chen, Q An, S D Gillies, High level expression and secretion of Fc-X fusion proteins in mammalian cells., *Protein Engineering, Design and Selection*, Volume 11, Issue 6, June 1998, Pages 495-500.

Longo, N. S., T. Rogosch, M. Zemlin, M. Zouali and P. E. Lipsky (2017). "Mechanisms That Shape Human Antibody Repertoire Development in Mice Transgenic for Human Ig H and L Chain Loci." J Immunol 198(10): 3963-3977.

McConnell, A. D., V. Spasojevich, J. L. Macomber, I. P. Krapf, A. Chen, J. C. Sheffer, A. Berkebile, R. A. Horlick, S. Neben, D. J. King and P. M. Bowers (2013). "An integrated approach to extreme thermostabilization and affinity maturation of an antibody." Protein Eng Des Sel 26(2): 151-164.

Mitchell, L. S., and L. J. Colwell (2018). "Comparative analysis of nanobody sequence and structure data." Proteins 86(7): 697-706. Muyldermans, S. (2013). "Nanobodies: natural single-domain antibodies." Annu Rev Biochem 82: 775-797.

Nguyen, V. K., Hamers, R., Wyns, L., and Muyldermans, S. (2000). Camel heavy-chain antibodies: diverse germline VHH and specific mechanisms enlarge the antigen-binding repertoire. EMBO J. 19, 921-930.

Nguyen, V. K., Hamers, R., Wyns, L., and Muyldermans, S. (1999). Loss of splice consensus signal is responsible for the removal of the entire CH1 domain of the functional camel IgG2a heavy chain antibodies. Mol Immunol. 36, 515-24.

Rossotti, M. A., Belanger, K., Henry, K. A., Tanha, J. (2021). Immunogenicity and humanization of single-domain antibodies. FEBS J. 15809.

Saerens D, Pellis M, Loris R, Pardon E, Dumoulin M, Matagne A, Wyns L, Muyldermans S, Conrath K. Identification of a universal VHH framework to graft non-canonical antigen-binding loops of camel single-domain antibodies. J Mol Biol 2005; 352:597-607

Shi, L., J. C. Wheeler, R. W. Sweet, J. Lu, J. Luo, M. Tornetta, B. Whitaker, R. Reddy, R. Brittingham, L. Borozdina, Q. Chen, B. Amegadzie, D. M. Knight, J. C. Almagro, and P. Tsui (2010). "De novo selection of high-affinity antibodies from synthetic fab libraries displayed on phage as pIX fusion proteins." J Mol Biol 397(2): 385-396.

Slastnikova, T. A., A. V. Ulasov, A. A. Rosenkranz and A. S. Sobolev (2018). "Targeted Intracellular Delivery of Antibodies: The State of the Art." Front Pharmacol 9: 1208.

Suckling, L., C. McFarlane, C. Sawyer, S. P. Chambers, R. I. Kitney, D. W. McClymont and P. S. Freemont (2019). "Miniaturisation of high-throughput plasmid DNA library preparation for next-generation sequencing using multifactorial optimisation." Synth Syst Biotechnol 4(1): 57-66.

Tiller, T., I. Schuster, D. Deppe, K. Siegers, R. Strohner, T. Herrmann, M. Berenguer, D. Poujol, J. Stehle, Y. Stark, M. HeBling, D. Daubert, K. Felderer, S. Kaden, J. Kölln, M. Enzelberger and S. Urlinger (2013). "A fully synthetic human Fab antibody library based on fixed VH/VL framework pairings with favorable biophysical properties." mAbs 5(3): 445-470.

Tonikian, R. and S. S. Sidhu (2012). "Selecting and purifying autonomous human variable heavy (VH) domains." Methods Mol Biol 911: 327-353.

Vincke C, Loris R, Saerens D, Martinez-Rodriguez S, Muyldermans S, Conrath K. General strategy to humanize a camelid single-domain antibody and identification of a universal humanized nanobody scaffold. J Biol Chem 2009; 284:3273-84

Wilken, L., and A. McPherson (2018). "Application of camelid heavy-chain variable domains (VHHs) in prevention and treatment of bacterial and viral infections." Int Rev Immunol 37(1): 69-76.

Winter, G., A. D. Griffiths, R. E. Hawkins, and H. R. Hoogenboom (1994). "Making antibodies by phage display technology." Annu Rev Immunol 12: 433-455.

Wrapp, D., D. De VLieger, K. S. Corbett, G. M. Torres, W. Van Breedam, K. Roose, L. van Schie, M. Hoffmann, S. Pöhlmann, B. S. Graham, N. Callewaert, B. Schepens, X. Saelens and J. S. McLellan (2020). "Structural Basis for Potent Neutralization of Betacoronaviruses by Single-domain Camelid Antibodies." bioRxiv: 2020.2003.2026.010165.

Wu, Y., Li, C., Xia, S., Tian, X., Kong, Y., Wang, Z., Gu, C., Zhang, R., Tu, C., Xie, Y., Yang, Z., Lu, L., Jiang, S., Ying, T. (2020). Identification of human single domain antibodies against SARS-CoV-2. Cell Host and Microbe, 27, 891-898.

Yan J, Li G, Hu Y, Ou W, Wan Y. Construction of a synthetic phage-displayed nanobody library with CDR3 regions randomized by trinucleotide cassettes for diagnostic applications. J Transl Med 2014; 12:343

Yang, Y. S., K. D. Moynihan, A. Bekdemir, T. M. Dichwalkar, M. M. Noh, N. Watson, M. Melo, J. Ingram, H. Suh, H. Ploegh, F. R. Stellacci and D. J. Irvine (2018). "Targeting small molecule drugs to T cells with antibody-directed cell-penetrating gold nanoparticles." Biomater Sci 7(1): 113-124.

1. U.S. Pat. No. 8,105,592 B2 HEAVY CHAIN AND SINGLE DOMAIN ANTIBODIES
2. CA 2380443 C 2013/03/12 SINGLE DOMAIN ANTIGEN BINDING ANTIBODY FRAGMENTS DERIVED FROM LLAMA ANTIBODIES
3. US 2020/0031952 A1 HIGH AFFINITY AND AGGREGATIVELY STABLE ANTIBODIES ON THE BASIS OF VARIABLE DOMAINS VL AND A DERIVATIVE VHH
4. WO2016072938A1 STABILIZED AND AUTONOMOUS ANTIBODY Vh DOMAIN
5. U.S. Pat. No. 9,062,305 B2 GENERATION OF HUMAN DE NOVO PIX DISPLAY LIBRARIES
6. US20050226863A1
7. EP2139918A2
8. EP2139918B1
9. AU2011200930A1
10. AU2011200930B2

We claim:

1. A VHO library of polynucleotides encoding VHO (variable heavy only) domains, wherein the VHO domains have sequence homology and/or canonical homology with the Vh domain of a human Vh family IGHV3-23 and comprise:

SEQ ID NO: 5:
(SEQ ID NO: 5)
QVQLVESGGGLVKPGGSLRLSCAASGFTFS(X)WVRQAPGKGLEWV(X)
DSVKGRFTISRDNSKNTLYLQMNSLRAEDTAVYYCAR(X)WGQGTLVTV
SS, or

SEQ ID NO: 6:
(SEQ ID NO: 6)
EVQLVESGGGLVQPGGSLRLSCAASGFTFS(X)NWVRQAPGKGLEWV
(X)DSVKGRFTISRDNSKNTLYLQMNSLRAEDTAVYYCAR(X)WGQG
TLVTVSS, wherein position X represents any one of the 20 naturally occurring amino acid residues.

2. The VHO library of claim 1, wherein the VHO domains have residue diversity in one or more of the CDR regions.

3. The VHO library of claim 1, wherein position X is replaced with an even distribution of all 20 naturally occurring amino acids except for C for CDR1, C and M for CDR2, and C, M, and N for CDR3.

4. The VHO library of claim 1, wherein the VHO domains have length diversity in the CDR3 region.

5. The VHO library of claim 1, wherein the length diversity of the CDR3 region ranges from 6 to 30 codons.

6. The VHO library of claim 1, wherein the polynucleotides encoding VHO domains are inserted into a vector.

7. The VHO library of claim 6, wherein the vector is a phagemid.

8. The VHO library of claim 6, wherein the vector is a plasmid.

9. The VHO library of claim 6, wherein the vector comprises polynucleotides encoding a coat protein of a bacterial phage.

10. The VHO library of claim 9, wherein the bacterial phage is M13 bacteriophage.

11. The VHO library of claim 10, wherein the coat protein is a pVII or pIX coat protein.

12. The VHO library of claim 6, wherein the vector comprises one or more tags.

13. The VHO library of claim 12, wherein the one or more tags are chosen from polyhistidine (HIS) and hemagglutinin (HA) tags.

14. The VHO library of claim 13, wherein the vector comprises a polynucleotide sequence encoding a linker peptide between the VHO and the one or more tags.

15. The VHO library of claim 13, wherein the vector comprises a polynucleotide sequence encoding a linker peptide between VHO and the coat protein.

16. The VHO library of claim 14, wherein the linker peptide is GGGGS (SEQ ID NO: 17).

17. The VHO library of claim 6, wherein the vector comprises elements that are arranged in a manner to allow for the VHO domains to be displayed on a bacteriophage.

18. The VHO library of claim 6, wherein the vector comprises elements that are arranged in a manner to allow for the VHO domains to be expressed.

19. The VHO library of claim 6, wherein the vector comprises elements that are arranged in a manner to allow for the VHO domains to be expressed without a bacterial phage.

20. The VHO library of claim 6, wherein the vector has Ori site for DNA replication, an Ori site for phage replication, a leader sequence for driving secretion of translated proteins, a promoter for driving protein expression, and a repressor to control levels of protein expression.

21. The vector of claim 6, wherein the vector comprises a polynucleotide encoding any one of the VHO domains.

22. A phage library displaying the VHO domains encoded by the VHO library of claim 1.

23. The phage library of claim 22, wherein the VHO domains are displayed on a viral particle produced by a prokaryotic or a eukaryotic cell, displayed on a virus that infects a prokaryotic and/or eukaryotic host cell, or displayed on a prokaryotic or a eukaryotic cell.

24. A method of preparing the VHO library of claim 1, comprising: providing polynucleotide sequences encoding VHO domains; and inserting the polynucleotide sequences a vector, wherein the VHO domains have sequence homology and/or canonical homology with the Vh domain of human Vh family IGHV3-23.

25. A method of preparing the phage library of claim 22, comprising: transforming a bacterial cell culture with a VHO library, allowing the bacterial cell culture to grow to a log phase, infecting the bacterial cell culture with a helper phage, and amplifying the bacterial cell culture, wherein the VHO library comprises polynucleotides encoding VHO (variable heavy only) domains, and wherein the VHO domains have sequence homology and/or canonical homology with the Vh domain of human Vh family IGHV3-23.

26. A method of identifying a VHO domain of interest that is capable of binding a target, comprising: creating a VHO library, creating a phage library of according to claim 25, and screening the phage library using biopanning against the target to identify the VHO of interest, wherein the VHO library comprises polynucleotides encoding VHO (variable heavy only) domains, and wherein the VHO domains have sequence homology and/or canonical homology with the Vh domain of human Vh family IGHV3-23.

27. The method of claim 26, wherein the biopanning step is conducted multiple times.

28. The method of claim 26, further comprising sequencing the VHO of interest by NGS.

29. The method of claim 26, further comprising evaluating the binding affinity of the VHO of interest to the target.

30. The method of claim 29, wherein the binding affinity is evaluated using ELISA.

31. A cell comprising the vector of claim 21.

* * * * *

SEQUENCE LISTING

```
<160> NUMBER OF SEQ ID NOS: 27

<210> SEQ ID NO 1
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: A, W, or Y
<220> FEATURE:
<221> NAME/KEY: MOD_RES
<222> LOCATION: (52)..(52)
<223> OTHER INFORMATION: I, N, or Y
<220> FEATURE:
<221> NAME/KEY: MOD_RES
<222> LOCATION: (54)..(54)
<223> OTHER INFORMATION: S, G, or D
<220> FEATURE:
<221> NAME/KEY: MOD_RES
<222> LOCATION: (57)..(57)
<223> OTHER INFORMATION: H, S, or T

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Xaa Met Ser Trp Val Arg Gln Ala Pro Gly Lys Gly Leu Glu Trp Val
        35                  40                  45

Ser Thr Ile Xaa Ser Xaa Gly Asp Xaa Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80
```

-continued

Gln Met Asn Ser Leu Lys Pro Glu Asp Thr Ala Val Tyr Tyr Cys Ala
                85                  90                  95

Ala

<210> SEQ ID NO 2
<211> LENGTH: 96
<212> TYPE: PRT
<213> ORGANISM: Homo sapiens

<400> SEQUENCE: 2

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Val Ile Ser Ser Lys Asp His Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

<210> SEQ ID NO 3
<211> LENGTH: 99
<212> TYPE: PRT
<213> ORGANISM: Unknown
<220> FEATURE:
<223> OTHER INFORMATION: Description of Unknown:
      Camel Vh domain

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Gly Ser
            20                  25                  30

Tyr Trp Met Tyr Trp Phe Arg Gln Ala Pro Gly Lys Gly Arg Glu Trp
        35                  40                  45

Val Ser Thr Ile Asn Thr Gly Gly Asp Ser Ser Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Val Tyr Tyr
                85                  90                  95

Cys Ala Ala

<210> SEQ ID NO 4
<211> LENGTH: 97
<212> TYPE: PRT
<213> ORGANISM: Unknown
<220> FEATURE:
<223> OTHER INFORMATION: Description of Unknown:
      Llama Vh domain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Thr Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala

<210> SEQ ID NO 5
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally occurring amino acid
<220> FEATURE:
<221> NAME/KEY: MOD_RES
<222> LOCATION: (45)..(45)
<223> OTHER INFORMATION: Any naturally occurring amino acid
<220> FEATURE:
<221> NAME/KEY: MOD_RES
<222> LOCATION: (83)..(83)
<223> OTHER INFORMATION: Any naturally occurring amino acid

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Xaa Trp
            20                  25                  30

Val Arg Gln Ala Pro Gly Lys Gly Leu Glu Trp Val Xaa Asp Ser Val
        35                  40                  45

Lys Gly Arg Phe Thr Ile Ser Arg Asp Asn Ser Lys Asn Thr Leu Tyr
    50                  55                  60

Leu Gln Met Asn Ser Leu Arg Ala Glu Asp Thr Ala Val Tyr Tyr Cys
65                  70                  75                  80

Ala Arg Xaa Trp Gly Gln Gly Thr Leu Val Thr Val Ser Ser
                85                  90

<210> SEQ ID NO 6
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally occurring amino acid
<220> FEATURE:
<221> NAME/KEY: MOD_RES
<222> LOCATION: (46)..(46)
<223> OTHER INFORMATION: Any naturally occurring amino acid
<220> FEATURE:
<221> NAME/KEY: MOD_RES
<222> LOCATION: (84)..(84)
<223> OTHER INFORMATION: Any naturally occurring amino acid

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Asn
            20                  25                  30

Trp Val Arg Gln Ala Pro Gly Lys Gly Leu Glu Trp Val Xaa Asp Ser
            35                  40                  45

Val Lys Gly Arg Phe Thr Ile Ser Arg Asp Asn Ser Lys Asn Thr Leu
    50                  55                  60

Tyr Leu Gln Met Asn Ser Leu Arg Ala Glu Asp Thr Ala Val Tyr Tyr
65                  70                  75                  80

Cys Ala Arg Xaa Trp Gly Gln Gly Thr Leu Val Thr Val Ser Ser
                85                  90                  95

<210> SEQ ID NO 7
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Ala Pro Gly Lys Gly Leu Glu Trp Val
            35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Lys Gly Ala Gly Arg Gly Pro Gly Ala Leu Gly Gly Leu
            100                 105                 110

Asp Val Trp Gly Gln Gly Thr Leu Val Thr Val Ser Ser
            115                 120                 125

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
            35                  40                  45

Ser Ala Ile Trp Ser Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Arg Thr Trp Gly His Gln Phe Asp Tyr Trp Gly Gln Gly Thr
            100                 105                 110

Leu Val Thr Val Ser Ser
        115
```

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Val Ile Asn Tyr Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Met Gly Thr Pro Gly Glu Leu Pro Leu Asp Tyr Trp Gly Gln Gly
            100                 105                 110

Thr Leu Val Thr Val Ser Ser
        115
```

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Gly Ile Ser Tyr Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Trp Ala Val Pro Gly Arg Gly His Pro Arg Phe Asp
            100                 105                 110

Tyr Trp Gly Gln Gly Thr Leu Val Thr Val Ser Ser
        115                 120
```

```
<210> SEQ ID NO 11
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Phe Asp Tyr Trp Gly Gln Gly Thr Leu Val Thr Val
            100                 105                 110

Ser Ser

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Gly Ser
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Ser
1

<210> SEQ ID NO 15
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Ser Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Gly Ser Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Gly Gly Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Ser Gly
```

1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Ser Ser Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Ala Ala Ala Lys
1               5

<210> SEQ ID NO 23
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: A, G, or Y
<220> FEATURE:
<221> NAME/KEY: MOD_RES
<222> LOCATION: (56)..(56)
<223> OTHER INFORMATION: G, S, or absent

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Xaa Met Ser Trp Val Arg Gln Ala Pro Gly Lys Gly Leu Glu Trp Val
        35                  40                  45

Ser Val Ile Tyr Ser Gly Gly Xaa Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 24
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 25
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 26
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Ile Gln Pro Gly Gly
1               5                   10                  15

Ser Leu Arg Leu Ser Cys Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala

<210> SEQ ID NO 27
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```